(12) United States Patent
Robinson

(10) Patent No.: US 8,877,453 B2
(45) Date of Patent: Nov. 4, 2014

(54) DIAGNOSING AND MANAGING VENOUS THROMBOEMBOLISM AND INTRACARDIAC THROMBI USING A PROVOKED D-DIMER TEST

(75) Inventor: Vincent J. B. Robinson, Martinez, GA (US)

(73) Assignee: Georgia Regents Research Institute, Inc., Augusta, GA (US)

( * ) Notice: Subject to any disclaimer, the term of this patent is extended or adjusted under 35 U.S.C. 154(b) by 0 days.

(21) Appl. No.: 13/400,818

(22) Filed: Feb. 21, 2012

(65) Prior Publication Data

US 2012/0270243 A1 Oct. 25, 2012

Related U.S. Application Data

(63) Continuation of application No. PCT/US2010/002265, filed on Aug. 18, 2010.

(60) Provisional application No. 61/342,692, filed on Apr. 16, 2010, provisional application No. 61/274,432, filed on Aug. 18, 2009, provisional application No. 61/274,429, filed on Aug. 18, 2009.

(51) Int. Cl.
*G01N 33/86* (2006.01)
*G01N 33/68* (2006.01)

(52) U.S. Cl.
CPC ...... *G01N 33/6893* (2013.01); *G01N 2800/226* (2013.01); *G01N 2800/32* (2013.01); *G01N 33/86* (2013.01)
USPC .......................................... 435/7.92; 435/7.1

(58) Field of Classification Search
CPC .. A61B 5/02007; A61B 5/412; A61B 5/7267; A61B 5/0059; A61B 6/481; A61B 6/482; A61B 6/504; A61B 5/02028; A61B 5/4528; A61B 5/7275; A61B 8/06; A61B 2560/0252; A61B 2560/0431; A61B 2560/0462; A61B 2560/046

See application file for complete search history.

(56) References Cited

U.S. PATENT DOCUMENTS 5,206,140 A 4/1993 Marder
2009/0305301 A1 12/2009 Mirshahi

OTHER PUBLICATIONS

Sherry et al., (Ann. Rev. Pharmacol. Toxicol. 1985; 25:413-31).*
Ibebuogu et al., (Can. J Cardiol; 2008;vol. 24 No. 6, pp. 517-519).*
Cushman, Fibrin fragment D-dimer and the risk of future venous thrombosis, journal, 2003, p. 1243-1248, vol. 101, Blood, US.
Robinson, Latex D-dimer Signal in In Situ Femoral Vein Thrombus in Swine and Effect of Minidose Exogenous Tissue Plasminogen Activator Bolus, journal, 2005, p. 622-629, vol. 127, Chest, US.
Hart,et al., "The detection of D-dimer in plasma by enzyme immunoassay: improved discrimination is obtained with a more specific signal antibody", Blood Coagul. Fibrinolysis, 5:227-32 (1994).

* cited by examiner

*Primary Examiner* — Shafiqul Haq
*Assistant Examiner* — Carmencita M Belei
(74) *Attorney, Agent, or Firm* — Pabst Patent Group LLP

(57) ABSTRACT

The present invention provides methods for diagnosing a venous thromboembolism or intracardiac thrombi in an individual in need of such treatment. A representative method of the present invention comprises the steps of: obtaining a plasma sample from said individual; determining the baseline level of D-dimer in said sample; contacting said sample with a compound that catalyzes the conversion of plasminogen into plasmin; and measuring the level of D-dimer is said sample after administering or contacting said sample with a compound that catalyzes the conversion of plasminogen into plasmin, wherein a significantly greater concentration of D-dimer after contact with a compound that catalyzes the conversion of plasminogen into plasmin than prior to contact with a compound that catalyzes the conversion of plasminogen into plasmin indicates that said individual has pulmonary embolism or venous thromboembolism.

3 Claims, 17 Drawing Sheets

DIAGNOSING AND MANAGING VENOUS THROMBOEMBOLISM AND INTRACARDIAC THROMBI USING A PROVOKED D-DIMER TEST

CROSS-REFERENCE TO RELATED APPLICATION

This is a continuation application under 35 U.S.C. §120 of pending international application PCT/US2010/002265, filed Aug. 18, 2010, which claims benefit of priority under 35 U.S.C §119(e) of provisional application U.S. Ser. No. 61/342,692, filed Apr. 16, 2010, provisional application U.S. Ser. No. 61/274,432, filed Aug. 18, 2009, and provisional application U.S. Ser. No. 61/274,429, filed Aug. 18, 2009, the entirety of all of which is hereby incorporated by reference.

BACKGROUND OF THE INVENTION

1. Field of the Invention

The present invention relates to the fields of diagnostic and therapeutic cardiology. More specifically, the present invention relates to, inter alia, methods for diagnosing and managing venous thromboembolism and intracardiac thrombi.

2. Description of the Related Art

Fibrinolysis is the process of degradation of fibrin in the blood. Fibrinolysis is involved in a number of physiopathological processes and is triggered in situations when tissue plasminogen activator (t-PA) and plasminogen bind to fibrin, forming a fibrin-plasminogen complex within which the t-PA has a high affinity for plasminogen, entraining the generation of plasmin, a key enzyme which degrades fibrin into D-dimers.

Degradation of fibrin, or fibrinolysis, leads to the formation of degradation products especially comprising "D-dimer" fragments, the major degradation products of cross-linked fibrin.

The fibrin undergoing the fibrinolysis process is formed by conversion of fibrinogen under the action of the coagulation enzyme thrombin. Upon activation of the coagulation system, thrombin cleaves fibrinogen, opening the polymerizing sites and generating fibrin soluble monomer along with fibrin protofibrils. To accomplish this, thrombin attacks four peptide bonds of the fibrinogen located respectively on the 2 A alpha and the 2 B beta chains, causing the liberation of two A fibrinopeptides from the two A alpha chains and the liberation of two B fibrinopeptides from the B beta chains, resulting in the formation of fibrin monomers which polymerize spontaneously into the form of a polymer by dint of hydrogen bonds established by interaction between A and B polymerization sites unmasked during liberation of the A and B fibrinopeptides and the a and b sites which are available at the ends of the gamma and beta chains respectively. The fibrin polymer is then immediately stabilized by factor XIII(a), forming insoluble cross-linked fibrin, the main component of thrombi. Thrombin generation is much greater during in vitro tests than that which takes place in vivo. For this reason, the generation of fibrin monomers is much slower in the in vivo coagulation activation process than in that generated in vitro.

Determining the concentration of soluble fibrin monomer of fibrinopeptides is important in order to estimate the degree of coagulation up-regulation in a patient. The increased level of soluble fibrin monomer will represent thrombin overactivity and will be associated with a cleavage of fibrinogen. This determination may be carried out using samples of blood or plasma obtained from a blood sample taken from a patient.

Assaying soluble fibrin monomer of fibrinopeptides is a useful complement to plasma fibrinolytic status since soluble fibrin monomer is a marker of thrombotic event and up-regulation of coagulation which is under way while the concentration of fibrin degradation products (particularly D-dimer) indicates degradation of a thrombus, even if the activation of coagulation process is stopped. In summary, the plasma level of fibrin degradation products or D-dimer is increased while the fibrin clot degrades in vivo. Hence, if the thrombus is present and undergoing degradation, the level of D-dimers is high, whether coagulation persists or is stopped. In contrast, the level of soluble fibrin is raised only if coagulation persists.

Commercially available D-dimer assays are limited to detection of only single D-dimer structure. The interference with other fibrin degradation products are mostly excluded as the antibody used is specific only for a neo-antigen on the D-Dimer structure. Thus, determining the level of D-dimers in the sample, termed the base level, is a reflection of the degradation of the thrombus which occurs in vivo, while further cleavage of soluble fibrin degradation products in vitro or in vivo with exogenic addition of a specific fibrin thrombolytic agent results in profound fibrinolysis and completed release of D-dimer from multimeric fibrin degradation products. The final level of D-dimer represents the sum of the base D-dimers and the D-dimers deriving from degradation of fibrin degradation products and soluble complexes of D-Dimer or fibrin degradation products with fibrin monomer, also termed circulating fibrin.

Venous thromboembolism (VTE) is a common but diagnostically challenging illness that can cause significant disability and death if not promptly diagnosed and effectively treated. About 2 to 3 million individuals in the US develop VTE every year and of those, 60,000 die, primarily from pulmonary embolism (PE). Acute PE is a common and often fatal disease with a mortality rate of 30% without treatment. While mortality can be reduced by prompt diagnosis and therapy, it is estimated that more than half of all patients with PE remain undiagnosed. The magnitude of VTE as a clinical problem can be attributed to gaps in the understanding of pathogenic mechanisms, the wide variety in patient presentations, and limited diagnostic and therapeutic options. The D-dimer test is currently used to diagnose VTE in clinical practice, which measures the dimeric forms of the fibrin degradation products using an antigen-antibody reaction.

In 2005, using a swine model, it was shown that mini-dose tPA could lyse in situ thrombus in the femoral vein of swine, allowing increased sensitivity of D-dimer for detecting in situ venous thrombus in swine. This, however, did not address the problem of diagnosing venous thromboembolism in humans. Currently in humans, the problem is poor specificity and poor positive predictive value of a positive current D-dimer test. This pig study was designed to improve sensitivity when D-dimer did not detect clot.

Thromboembolic venous diseases principally comprise venous thromboses of the limbs and pulmonary embolism, the latter resulting from a complication of the first thromboses. Venous thromboses other than those of the limbs are also encountered, since all venous territories can undergo a thrombosis. The renal veins and mesenteric veins can be cited in particular among those which are at the origin of pathologies. Thromboembolic diseases such as deep venous thrombosis (DVT) and/or pulmonary embolism (PE) are life-threatening diseases and represent a large proportion of the disabilities and deaths in industrialized countries, and establishing a diagnosis of these diseases is vital in completing investigations by imaging examinations such as ultrasound imaging for the diagnosis of venous thromboses and scintography or angiography to diagnose pulmonary embolisms. These imaging methods are expensive, carry significant morbidity and hence are deployed late in the diagnostic process. Since the disease process is so variable from asymptomatic to life threatening prompt and accurate diagnosis is vital and can improve mortality significantly.

As a result, there is a continuing need for defining a test allowing rapid diagnosis of thromboembolic disease in a patient, that diagnosis including the possibility of excluding that disease without necessarily having recourse to additional investigations. Thus, there is a continued need in the art for improved methods and therapies to diagnose and treat venous thromboembolism and intracardiac thrombi. The present invention fulfills this long standing need and desire in the art.

SUMMARY OF THE INVENTION

The present invention is directed to a method of diagnosing a venous thromboembolism or intracardiac thrombi in an individual in need of such treatment, comprising the steps of: obtaining a plasma sample from said individual; determining the baseline level of D-dimer in said sample; contacting said sample with a compound that catalyzes the conversion of plasminogen into plasmin; and measuring the level of D-dimer in said sample after contacting said sample with a compound that catalyzes the conversion of plasminogen into plasmin, wherein a significantly greater concentration of D-dimer after contact with a compound that catalyzes the conversion of plasminogen into plasmin than prior to contact with a compound that catalyzes the conversion of plasminogen into plasmin indicates that said individual has venous thromboembolism or intracardiac thrombi.

In another embodiment, the present invention provides a method of diagnosing a pulmonary embolism or venous thromboembolism or intracardiac thrombi in an individual in need of such treatment, comprising the steps of: obtaining a plasma sample from said individual; determining the baseline level of D-dimer in said sample; administering a compound that catalyzes the conversion of plasminogen into plasmin to said individual; and measuring the level of D-dimer is said sample after contacting the sample with a compound that catalyzes the conversion of plasminogen into plasmin, wherein a significantly greater concentration of D-dimer after contact with a compound that catalyzes the conversion of plasminogen into plasmin than prior to contact with a compound that catalyzes the conversion of plasminogen into plasmin indicates that the individual has pulmonary embolism or venous thromboembolism.

In yet another embodiment, the present invention provides a kit for diagnosing diagnosing a pulmonary embolism or venous thromboembolism in an individual using a method according to the present invention, comprising: anti-D-dimer monoclonal antibodies; a compound that catalyzes the conversion of plasminogen into plasmin; and if appropriate a negative control sample.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
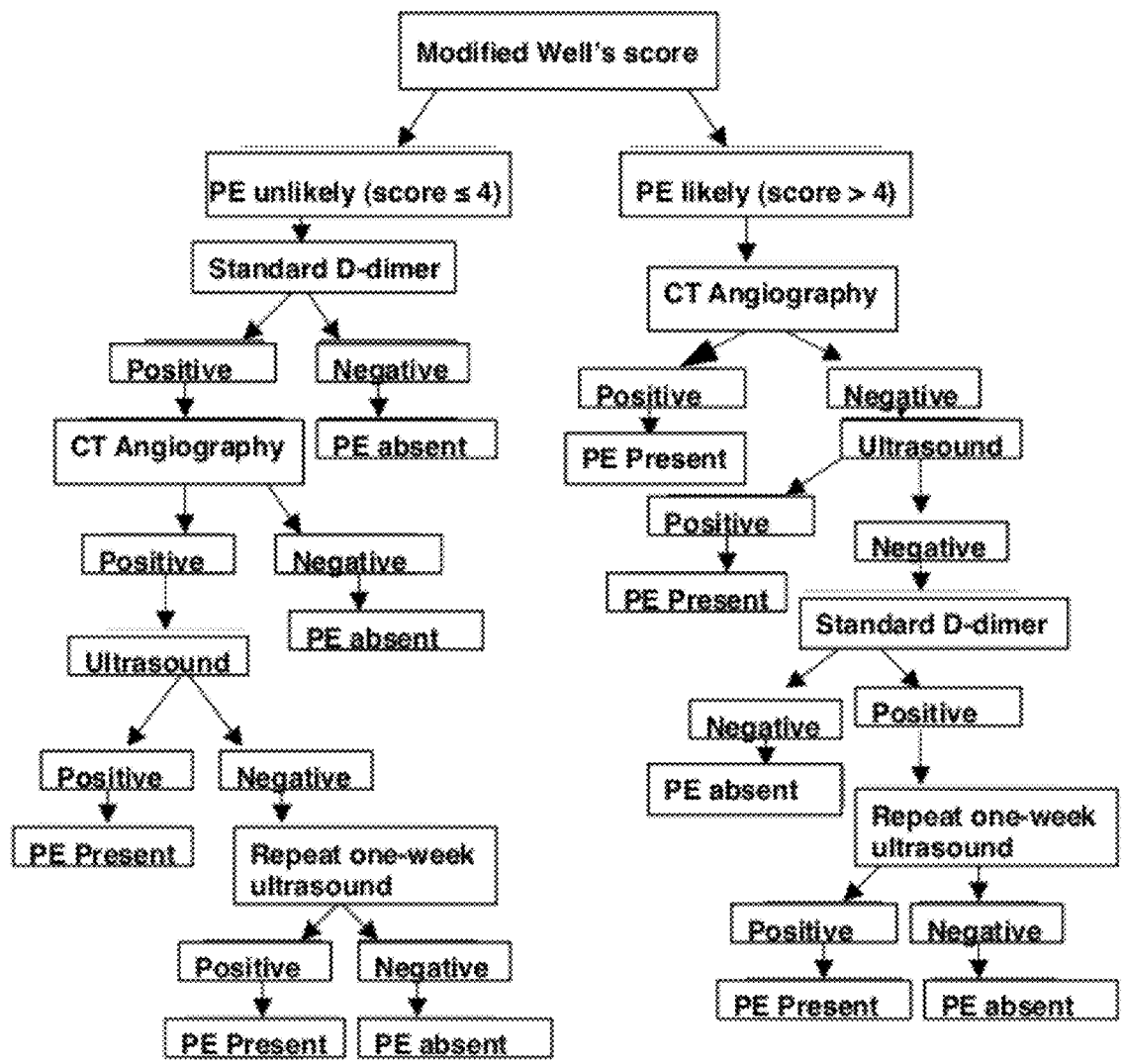
FIG. 1 depicts the currently recommended strategy for diagnosis of pulmonary embolisms. From Wells P., J Thromb Thrombolysis 21(1), 31-40, 2006.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein. As used herein, the term "or" in the claims refers to "and/or" unless explicitly indicated to refer to alternatives only or the alternatives are mutually exclusive, although the disclosure supports a definition that refers to only alternatives and "and/or". As used herein, the term "contacting" refers to any suitable method of bringing a compound or a composition into contact with a cell. In vitro or ex vivo this is achieved by exposing the cell to the compound or agent in a suitable medium. For in vivo applications, any known method of administration is suitable as described herein. As used herein, the term "subject" refers to any human or non-human recipient of the composition described herein.

The following example(s) are given for the purpose of illustrating various embodiments of the invention and are not meant to limit the present invention in any fashion. The present invention describes the development of a new "provoked" D-dimer test using a pilot study sample of patients with and without thromboemboli, as well as the feasibility of applying this novel test to prevent mortality and morbidity by facilitating earlier detection of human disease. These new tests can be performed both in vivo and in vitro.

Opportunity and Potential Impact

Venous thromboembolism is a common but elusive illness that can cause significant disability and death if not promptly diagnosed and effectively treated. Venous thromboembolism is significantly associated with increasing age, diabetes, and obesity. The rate ratios for the diagnosis of pulmonary embolism increases exponentially after age of 50 (6 fold over that of 20 year olds), increasing to almost 28 fold by the age of 80.

Deep vein thrombosis and acute pulmonary embolism are two manifestations of the same disorder, venous thromboembolism. This concept is supported by the fact that over 90 percent of cases of acute pulmonary embolism are due to emboli emanating from the proximal veins of the lower extremities. Over 50% of the venous thrombi are asymptomatic and the first manifestation of the disease may be death resulting from the obstruction of the pulmonary artery by the dislodged clot. Pulmonary embolism is associated with a mortality rate of approximately 30% without treatment, primarily the result of recurrent embolism. However, accurate diagnosis followed by effective therapy with anticoagulants decreases the mortality rate to 2-8%. [1-8] Mortality is strongly associated with advancing age as well as the presence of cardiovascular disease. Unfortunately, the clinical presentation of pulmonary embolism is variable and nonspecific, making accurate diagnosis difficult. There are several diagnostic options currently available but unfortunately due to intrinsic limitations, they are not clinically effective, forcing a reliance on a complex algorithm for the accurate diagnosis of venous thromboembolism.

D-Dimer and Pulmonary Embolism

The D-dimer test, currently used to diagnose venous thromboembolism in clinical practice, measures the final dimeric form of fibrin clot degradation using an antigen-antibody reaction. In the clinical setting, however, the D-dimer test suffers from poor specificity (35%) but has good sensitivity (95%) and negative predictive value (95%). The D-dimer signals can be elevated despite the absence of a fibrin clot in several conditions, such as sepsis, ischemia, malignancy, or renal/hepatic failure]. In addition, the reduced specificity deteriorates further in patients with higher clinical probability of venous thromboembolism. Taken together, these findings suggest that an elevated D-dimer level (>500 ng/mL) is not sufficient to diagnose pulmonary embolism, necessitating further testing to definitively diagnose pulmonary embolism (FIG. 1). On the other hand, due to the high negative predictive value, if the D-dimer level is <500 ng/mL, it excludes pulmonary embolism unless the pretest probability of pulmonary embolism is high.

Clinical Probability Assessment: (Table 1)

Several studies have suggested that commonly used imaging modalities in the evaluation of pulmonary embolism (Computed tomography angiography with venous phase imaging [CTAV] or ventilation/perfusion scan [V/Q scan]) require concomitant clinical probability assessment, most commonly the Wells model, to be effective diagnostic tools in detecting pulmonary embolism.

TABLE 1

Modified Wells' Model

| Variables used to determine patient pretest probability of PE | Score (points) |
| --- | --- |
| 1. Clinical symptoms of DVT (Leg swelling, pain with palpation) | 3.0 |
| 2. Alternative diagnosis less likely than PE | 3.0 |
| 3. Heart rate >100 | 1.5 |
| 4. Immobilization (>3 days) or surgery in the previous four weeks | 1.5 |
| 5. Previous DVT/PE | 1.5 |
| 6. Hemoptysis | 1.0 |
| 7. Malignancy | 1.0 |

Simplified Method: "PE unlikely" ≤4.0 and "PE likely" >4.0;
Traditional method: low probability <2.0, moderate probability 2.0-6.0, high probability >6.0.

Computed Tomography Angiography (CTA), with Venous Phase Imaging (CTAV):

Due to its widespread availability and the ability to detect alternative pulmonary abnormalities that may explain the patient's clinical presentation, computed tomography angiography with venous phase imaging is increasingly being used for patients with suspected pulmonary embolism. Additional advantages and disadvantages of CTAV are described in table 2. The largest study to date (824 patients) of computed tomography angiography with and without clinical probability assessment (using the Wells criteria) demonstrates that results should be interpreted with caution if the clinical probability of pulmonary embolism and computed tomography angiography results are discordant. Therefore, a negative computed tomography angiography is sufficient to exclude pulmonary embolism unless the clinical suspicion for pulmonary embolism is high.

Ventilation Perfusion (V/Q) Scans

In the most extensive evaluation of the accuracy of V/Q scans, the diagnostic accuracy was greatest when the V/Q scan was combined with clinical probability. Unfortunately, discordant combination of clinical and V/Q scan probabilities found in many patients (up to 72 percent) had a diagnostic accuracy of only 15 to 86 percent, which is insufficient to either confirm or exclude the diagnosis of pulmonary embolism. Therefore, computed tomography angiography with venous phase imaging is preferred over V/Q scan in computed tomography angiography experienced institutions due to its many advantages.

Ultrasound (US)

Although over 90% of cases of acute pulmonary embolism are due to emboli originating from the proximal veins of the lower extremities, some high-risk patients (e.g. elderly, after major surgery) develop deep vein thrombosis without local signs and symptoms hence would not receive a lower extremity ultrasound. Such patients may present with sudden and often fatal pulmonary embolism.

Currently Recommended Strategy for Diagnosis of PE: (FIG. 1)

To summarize, a D-dimer assay can be the first objective test used in addition to clinical assessment in determining which patients require diagnostic imaging. With current multi-detector scanners, the sensitivity of computed tomography angiography with venous phase imaging is improved. Without the consideration of clinical probability or the D-dimer test, CTAV and V/Q scans would yield a false positive result in approximately 5% and 10% of cases respectively. These false positives result in at least six months of unnecessary oral anticoagulation therapy, with its associated cost and complications. On the other hand, in the largest prospective computed tomography angiography study, 15% of patients had a positive ultrasound study despite a negative computed tomography angiography. Whenever the clinical probability and computed tomography angiography results are discordant, confirmatory serial bilateral complete deep vein ultrasound or conventional pulmonary angiography should be considered (FIG. 1).

Figure 2:
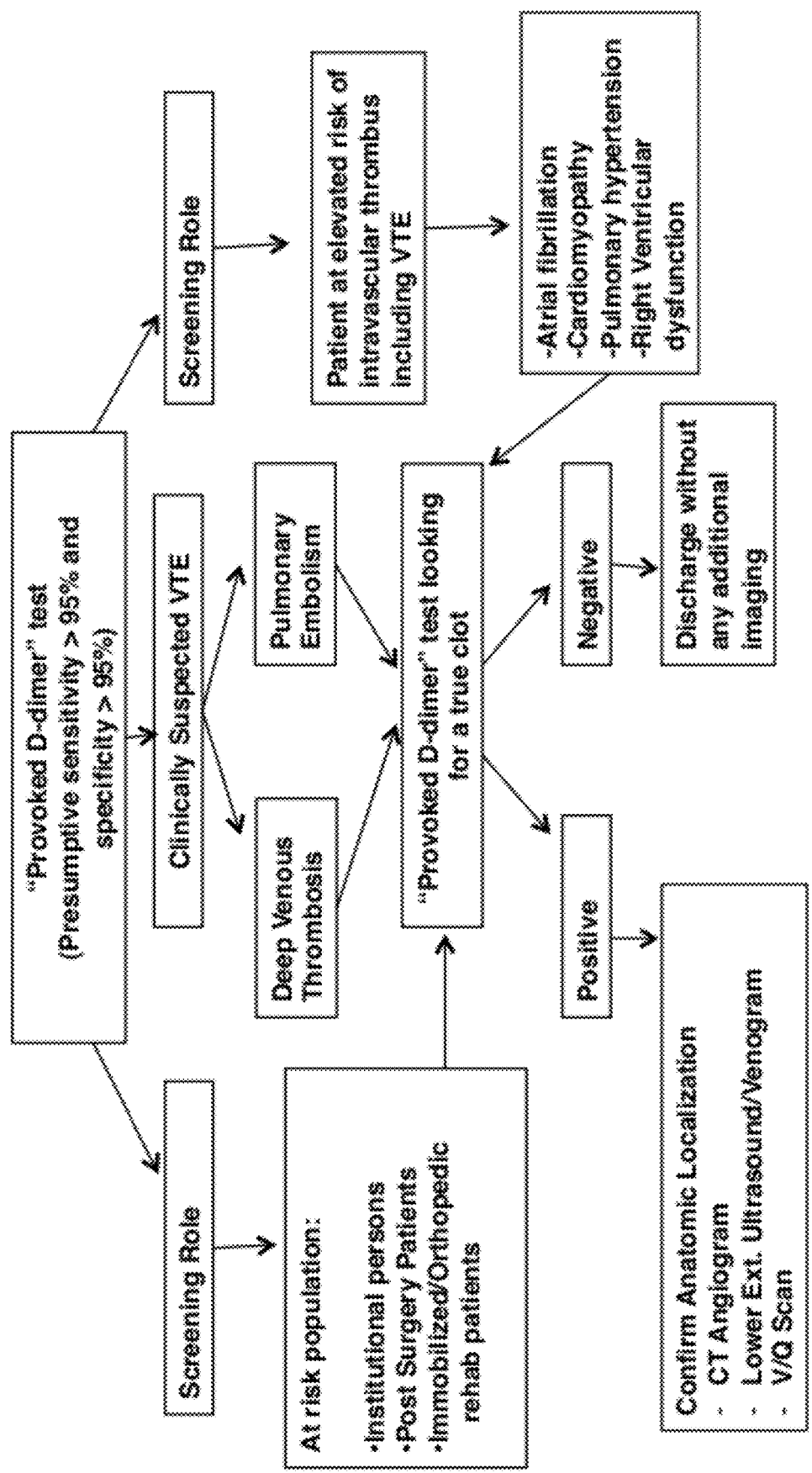
FIG. 2 illustrates the potential utility of the "Provoked D-dimer" test in screening and diagnosis of venous thromboembolism (VTE) in at-risk populations.

Potential Impact on Clinical Practice: (FIG. 2)

As outlined above, the current D-dimer test has low specificity and therefore abnormal D-dimer results are not sufficient to diagnose pulmonary embolism. Therefore, further testing is necessary to identify pulmonary embolism accurately. As per current clinical practice (FIG. 1), computed tomography angiography is the next recommended test. Several large trials involving computed tomography angiography and pulmonary embolism found that only 20-30% of CTA's are positive. Therefore, 70-80% of patients are exposed to the risks associated with computed tomography angiography unnecessarily. Older persons also have numerous co-morbidities, including chronic renal impairment, limiting the use of CTAV and increasing the risk of contrast nephrotoxicity.

Hence, in these circumstances, a new test with a higher specificity for true pulmonary embolism could exclude many false positive D-dimer tests and the use of many unnecessary CTAV's. Thus, the present invention can be useful in reducing the cost and morbidity related to the overuse of CTAV. A European study on the incidence of venous thromboembolism in older persons showed that up to 15% of asymptomatic older persons in sub-acute care settings were positive for venous thromboembolism on rigorous assessment and testing. The methods of the present invention could also improve the mortality related to pulmonary embolism by providing a quicker and more accurate noninvasive screening tool for such patients (FIG. 2) and therefore could result in a significant alleviation of the disease burden of venous thromboembolism.

Preliminary data confirms that the provoked D-dimer test can be performed both in vivo and in vitro with promising results. With the burden of venous thromboembolism affecting primarily older and frail asymptomatic individuals with multiple co-morbidities, a precise non-invasive test for venous thromboembolism could be deployed without the need for even a hospital visit. Hence if the in vitro provoked D-dimer test is of equal efficacy to the in vivo technique in the above mentioned population, then it will become the test of choice. Since pulmonary embolism is a lethal disorder, there is a low tolerance for missed diagnosis and if in vivo provocation is required to make the diagnosis in this older population, then it may become the test of choice.

Potential Economic Impact: (Table 2)

The cost analysis in a hypothetical cohort of 1000 patients receiving CTAV with suspected pulmonary embolism is described in Table 2. Considering a prevalence of pulmonary embolism of 20%, 800 patients would not have pulmonary embolism. Consider testing all 1000 patients of suspected pulmonary embolism by a standard D-dimer test (60 USD including professional fee to perform ELISA) followed by CTAV (850 USD including Medicare allowed professional fee to interpret CTAV) in instances of a positive D-dimer test. If the specificity of the current D-dimer is 35%, out of 800 patients without pulmonary embolism, D-dimer will be negative in 280 patients and falsely positive in 520 patients. This would lead to 520 unnecessary and hence avoidable CTAV's that would cost 442,000 USD. If the new test has a specificity of 95%, it would lead to only 40 negative and hence avoidable CTAV costing only 34,000 USD. Note that the total cost of the new test ($60 for an extra D-dimer assay and $15 for t-PA) for all 1000 patients would be 75,000 USD. Therefore, compared to the current D-dimer test, the net saving would be 333,000 USD if the "provoked" D-dimer test improved specificity to 95%. Similarly, as explained in Table 2, the net cost saving per 1000 patients would be 197,000 USD if specificity of the new test was improved to only 75%. In these calculations, the cost of morbidity attributable to the complications of CTAV e.g. contrast allergy and acute contrast-induced renal failure has not been included.

TABLE 2

Projected cost impact of anticipated improved specificity cut points of the new in vitro "Provoked" D-dimer test in patients with suspected PE

| 1000 patients with suspected PE, PE prevalence 20% (i.e. 800 without the PE) | Specificity of current "standard" D-dimer test | New specificity cut points potentially achieved with the new "provoked" D-dimer test | |
|---|---|---|---|
| Specificity | 35% | 75% | 95% |
| Negative D-dimer tests | 280 | 600 | 760 |
| False Positive (FP) D-dimer tests | 520 | 200 | 40 |
| Numbers of avoidable CTAs being done due to FP D-dimer | 520 | 200 | 40 |
| Cost related to all avoidable CTA ($850 each) | $442,000 | $170,000 | $ 34,000 |
| Additional cost of the new "Provoked" D-dimer test ($75 each) | $    0 | $ 75,000 | $ 75,000 |
| Total cost (avoidable CTA and the new provoked D-dimer) | $442,000 | $245,000 | $109,000 |
| Net cost saving by using the new provoked D-dimer test per 1000 patients | $    0 | $197,000 | $333,000 |

Approach:

The D-dimer test, currently used to diagnose venous thromboembolism in clinical practice, measures the dimeric forms of fibrin degradation products using an antigen-antibody reaction. Recombinant tissue-type plasminogen activator (t-PA) is a serine protease enzyme which converts plasminogen to plasmin. This initiates local fibrinolysis and digests fibrin ultimately into dimeric forms, which can be measured as D-dimer levels by different assays. In the clinical setting, the D-dimer test suffers from poor specificity (35%), leading to many false positives and thus requiring unnecessary, expensive, and potentially harmful additional imaging studies to confirm the diagnosis of venous thromboembolism. To address the issue of poor specificity, the present invention provides a "provoked" D-dimer test which more accurately detects true fibrin clots compared to the current standard D-dimer test in humans. The "provoked" D-dimer is defined as the amplified baseline (standard) D-dimer signal due to administration of t-PA either in vivo or in vitro. For the purpose of evaluating this new test, we propose analysis based on the following two equations:

Net Provoked Ddimer ($NPDD$) test =

(Provoked $Ddimer$ value) − (Standard $Ddimer$ value)

Percent "Provoked" $Ddimer$ ($PPDD$) test =

$$\left(\frac{\text{Net Provoked } Ddimer \text{ value}}{\text{Standard } Ddimer \text{ value}}\right) \times 100$$

Both in vivo and in vitro provocation may be performed in all patients. The in vivo technique represents the optimal experimental strategy for provocation as the exogenous t-PA is able to partially lyse the endogenous clot. The in vitro technique, however, allows for a totally noninvasive deployment of the "provoked" D-dimer test.

It is an object of the present invention to determine the ability of in vitro and in vivo exogenous mini-dose t-PA to amplify the standard D-dimer signal in patients with suspected pulmonary embolism.

It is another object of the present invention to compare the specificity, sensitivity and accuracy of the in vitro and in vivo "provoked" D-dimer (PDD) test with each other and to the current standard D-dimer (SDD) test in patients with suspected pulmonary embolism.

Experimental Support

A pilot in vitro study was performed in which 12 mL of blood was collected from five human subjects with and four human subjects without deep vein thrombosis and spun down. The plasma samples were divided into six equal aliquots of 1 mL. To these aliquots, five log doses of t-PA ranging from 0.00067 to 6.7 µg diluted in 1 mL of sterile water were added. One milliliter of only sterile water was added to the sixth aliquot to measure the baseline D-dimer (SDD). The D-dimer Enzyme Linked ImmunoSorbent Assay (ELISA) was performed on all samples and D-dimer levels calculated from the standard curve.

Figure 3:
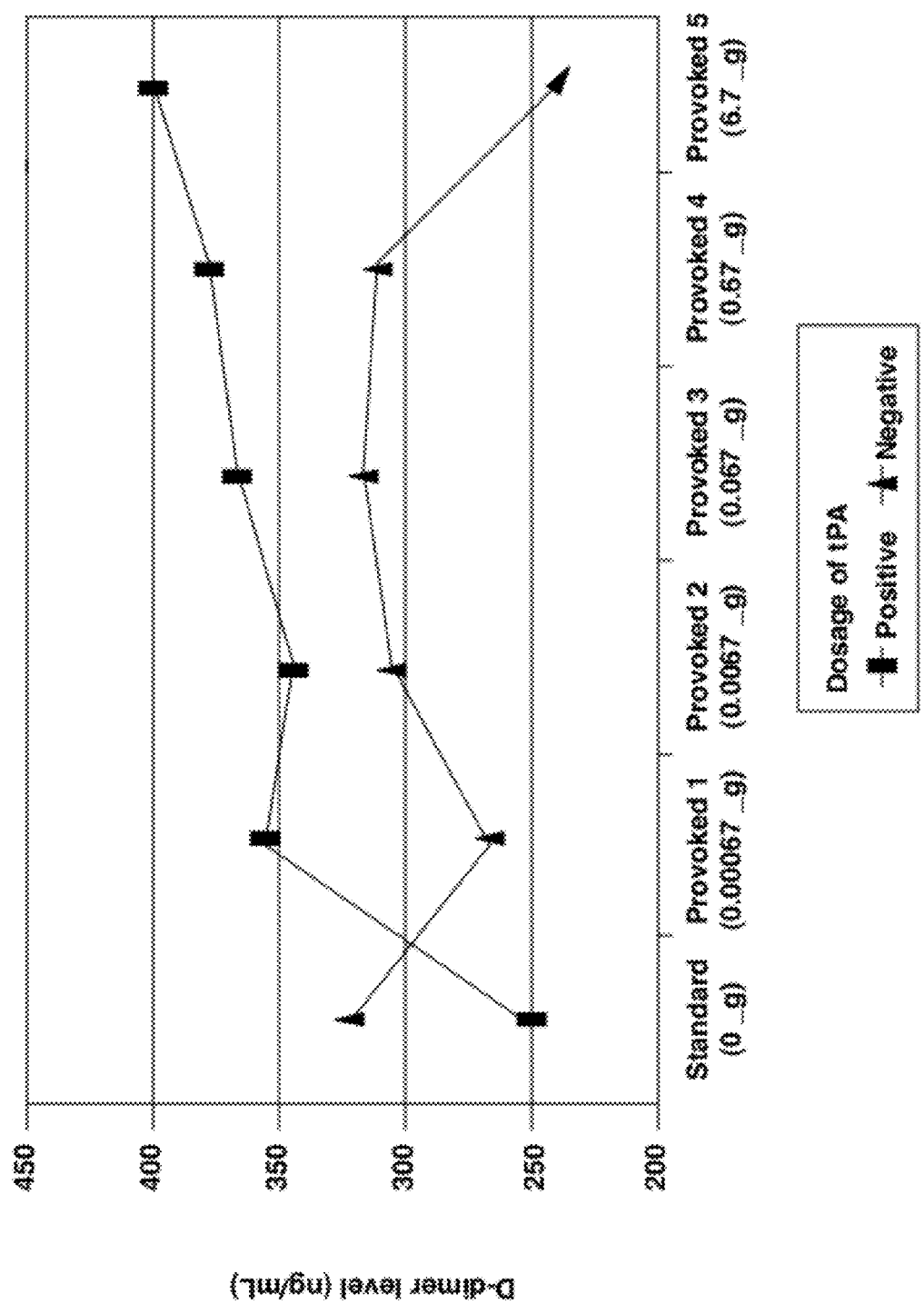
FIG. 3 shows a dose response of D-dimer levels to t-PA (in vitro) of plasma from patients with and without DVT.

The addition of exogenous t-PA to plasma from patients with deep vein thrombosis resulted in a significant increase in the mean D-dimer signal at all doses, with the highest increase in the highest dose (paired 1 tail t-test, $p=0.012$), while none of the dosages increased the mean D-dimer signal above the baseline in patients without deep vein thrombosis (paired 1 tail t-test, $p=0.270$). The net provocation rose as exogenous t-PA dose increased (FIG. 3). These results are consistent with an understanding that in vitro provocation is confined only to patients with proven venous thromboembolism due to the presence of further degradable tetramers and trimers in their plasma.

In vivo provocation was also performed in two patients with acute deep vein thrombosis achieving a 20% to 100% increase in D-dimer signal measured 45 minutes after intravenous injection of 2 mg t-PA.

Rationale to Overcome Existing Barriers in the Diagnosis of PE

Based on the in vitro pilot experiment in humans, the "provoked" D-dimer test may be a better diagnostic tool for PE/VTE than the current standard D-dimer test by eliminating its deficiencies. First, an abnormal D-dimer result is not sufficient to diagnose pulmonary embolism due to many false positive test results. With the "provoked" D-dimer test, only minor degree of amplification in the D-dimer signal is expected to occur in the absence of fibrin clot. This amplification of standard D-dimer is significantly more in the presence of true fibrin clot. Thus, the "provoked" D-dimer test is a useful test to exclude a false positive standard D-dimer test which is the most important limiting factor in the clinical utility of the standard D-dimer test.

Secondly, D-dimer levels are abnormal in 95 percent of patients with pulmonary embolism. In five percent of the patients with true venous thromboembolism, standard D-dimer remains falsely normal which may be due to an impaired ability of a subject to lyse any present clot effectively. There is also evidence that older persons have low endogenous tissue plasminogen activator levels resulting in lower sensitivity of the D-dimer test for DVT. Therefore, in elderly individuals, if there is true fibrin clot present, administration of t-PA should amplify the standard D-dimer signal significantly due to enhanced fibrinolysis. In this circumstance, the "provoked" D-dimer test is useful in excluding false negative D-dimer tests.

Thus, the "provoked" D-dimer test appears to be useful in improving both the sensitivity and specificity of the standard D-dimer test in patients with suspected venous thromboembolism. The present invention represents a new approach to the diagnosis of pulmonary embolism. This novel approach has been developed using existing available technology and thrombolytic agents, explored in preliminary human studies, and has the potential to reduce morbidity and mortality in patients with venous thromboembolism. This noninvasive test can potentially be used as screening tool in a frail, elderly population who are at increased risk and has potential to markedly reduce health care costs of venous thromboembolism by reducing unnecessary expensive tests e.g. CTAV.

Figure 4:
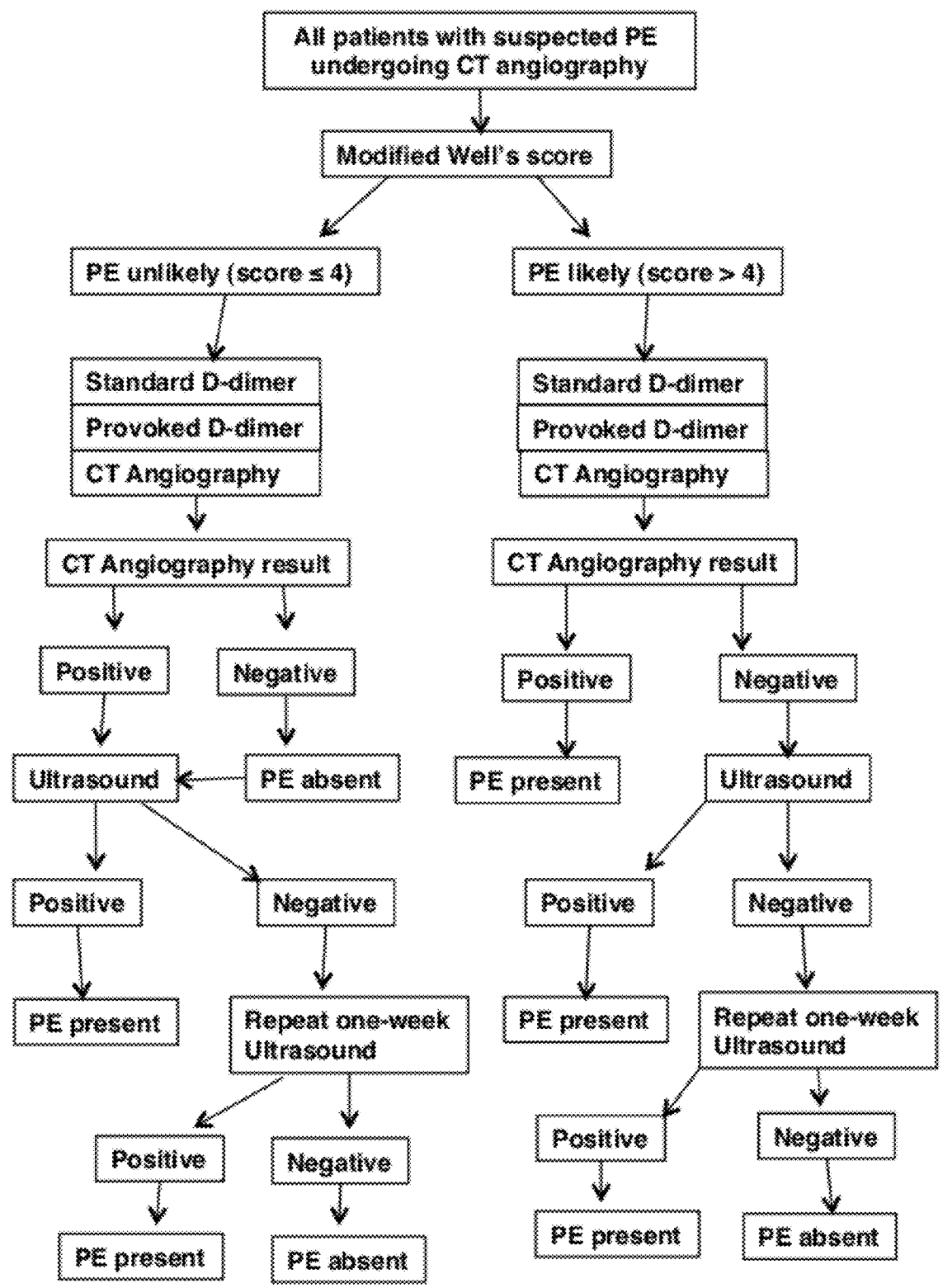
FIG. 4 shows a study algorithm useful in the methods of the present invention.

Study Design: (FIG. 4)

A non-randomized, consecutive sample, experimental trial is conducted. A total of 600 patients receiving CTAV for clinically suspected pulmonary embolism over 3 years are recruited at the Medical College of Georgia (MCG) Hospital in Augusta, Ga. All patients are recruited from the emergency room, hospital wards or clinics. The modified Wells score, CTAV and lower extremity venous ultrasound (US) is used concomitantly to identify the presence or absence of PE/VTE as illustrated in FIG. 4. The study algorithm has been designed to allow for a definitive identification of pulmonary embolism or deep vein thrombosis in all study participants who may or may not have a positive "provoked" D-dimer test.

All subjects with the possibility of a clot anywhere in the body except in the lower extremities and pulmonary vasculature based on history and physical examination are excluded. Also, all subjects on coumadin or heparin for >48 hours are excluded. In addition, any patient who is identified to have an increased bleeding risk based on history, physical examination or laboratory tests is excluded.

Study Protocol

The following steps will be performed in sequence, as follows:

1. Identify patients receiving CTAV for clinically suspected PE.
2. Obtain patient consent
3. Draw 12 mL of blood in a blue top test tube (citrated) for baseline D-dimer, CBC, PT, INR, PTT, fibrinogen, fibrinogen degradation products (FDP) tests and for in vitro D-dimer provocation.
4. Inject 4 mg t-PA into the antecubital vein and flush with 5 ml of normal saline.
5. Draw 6 ml of citrated venous blood at 15, 45 and 60 minutes after t-PA administration for in vivo provoked D-dimer levels and post provocation CBC, PT, INR, PTT, fibrinogen and FDP values at 90 minutes only.
6. Deliver blood samples to the lab supervisor to effect the blinded storage of the sample at −20° C.
7. Retrieve the numbered, blinded test tubes and thaw the samples in a body temperature water bath
8. Divide the baseline samples into 5 equal aliquots for in vitro testing.
9. Place 0, 0.0000067, 0.00067, 0.067, and 6.7 µg of t-PA in the aliquots, sequentially, and incubate for 1 hour.
10. Perform the ELISA D-dimer assay to determine the Standard D-dimer (SDD) level in the well with "0" µg of t-PA and the Provoked D-dimer levels in the wells with increasing t-PA concentration, in triplicate.
11. Perform ELISA on post t-PA injection samples to obtain in vivo provoked D-dimer measurements at 15, 45 and 60 minutes, in triplicate.

12. Perform statistical analyses to determine the optimal dose in vitro and optimal time in vivo of t-PA for provocation and the optimal cut off value for highest sensitivity and specificity in identifying PE.

Statistical Methods

Standard descriptive statistics are calculated for all demographic and clinical variables to describe the study population. Quantitative descriptive measures include means/medians, standard deviations, ranges, and 95% confidence intervals for means/medians; categorical descriptive measures include frequency counts, modes, percentages, and 95% confidence intervals for proportions.

In this comparative effectiveness assessment of two diagnostic tests, the standard approach is to assess each test's performance compared to a "gold" standard. There are four diagnostic tests to be conducted for each study subject with each compared to the "gold" standard consisting of definitive diagnosis of PE:

In Vitro:
1. Standard D-dimer (SDD) Test before t-PA administration
2. "Provoked" D-dimer (PDD) Test after t-PA administration at four different dosages. The "provoked" D-dimer (PDD) test is analyzed in 2 ways as following:
   a. Net "Provoked" D-dimer (NPDD) test=PDD level−SDD level.
   b. Percent "provoked" D-dimer (PPDD) test=(NPDD level)/(SDD level)×100%.

In Vivo:
3. Standard D-dimer (SDD) Test before t-PA administration
4. "Provoked" D-dimer (PDD) Test after t-PA administration at three different time points The "provoked" D-dimer (PDD) test is analyzed in 2 ways as following:
   a. Net "Provoked" D-dimer (NPDD) test=PDD level−SDD level.
   b. Percent "provoked" D-dimer (PPDD) test=(NPDD level)/(SDD level)×100%.

Receiver Operating Characteristics (ROC) analyses is conducted for Standard D-dimer, NPDD, and PPDD at all t-PA dosages for the in vitro measures and at all time points for the in vivo measures to determine the cut-point for optimal specificity for the highest sensitivity. The area under the curve (AUC) of these ROCs is compared using standard statistical procedures (sensitivity and specificity) for correlated binomial proportions. The major comparisons of interest consist of comparing the in vitro provoked D-dimer and in vivo provoked D-dimer measures and both to the Standard D-dimer for diagnostic test accuracy (sensitivity, specificity, and ROC AUC).

The inventors reviewed 359 consecutive cases of patients at the Emergency Department of the Medical College of Georgia who underwent CTAV for suspected pulmonary embolism from Aug. 1, 2004-Jul. 31, 2005. The yield of positive CTAV for pulmonary embolism was 7%. The hospitalized population has a higher incidence of pulmonary embolism (20-30%). If one assumes that 10% of those meeting inclusion criteria will truly have pulmonary embolism then for 600 total subjects recruited over 3 years, we will find 60 with pulmonary embolism (cases) and 540 without pulmonary embolism (controls).

A sample of 60 from the positive group and 540 from the negative group achieves 80% power to detect a difference of 0.15 between a diagnostic test with an area under the ROC curve (AUC) of 0.75 and another diagnostic test with an AUC of 0.90 using a two-sided z-test at a significance level of 0.05.

A sample size of 600 pairs achieves 80% power to detect an odds ratio of 2.0 using a two-sided McNemar test with a significance level of 0.05. The odds ratio is equivalent to a difference between two paired proportions (either sensitivity or specificity) of 0.067 which occurs when the proportion of discordant pairs is 0.20.

Thus, a sample size of 600 subjects (540 normal, 60 diseased) is required for two-sided tests, at the 0.05 significance level, comparing the AUC of two ROC curves or of comparing two paired measures of sensitivity (or two measures of specificity) with a power of at least 80% to detect clinically important differences.

Anticipated Results and Interpretation: (FIGS. 5, 6, 7, 8)

Figure 5:
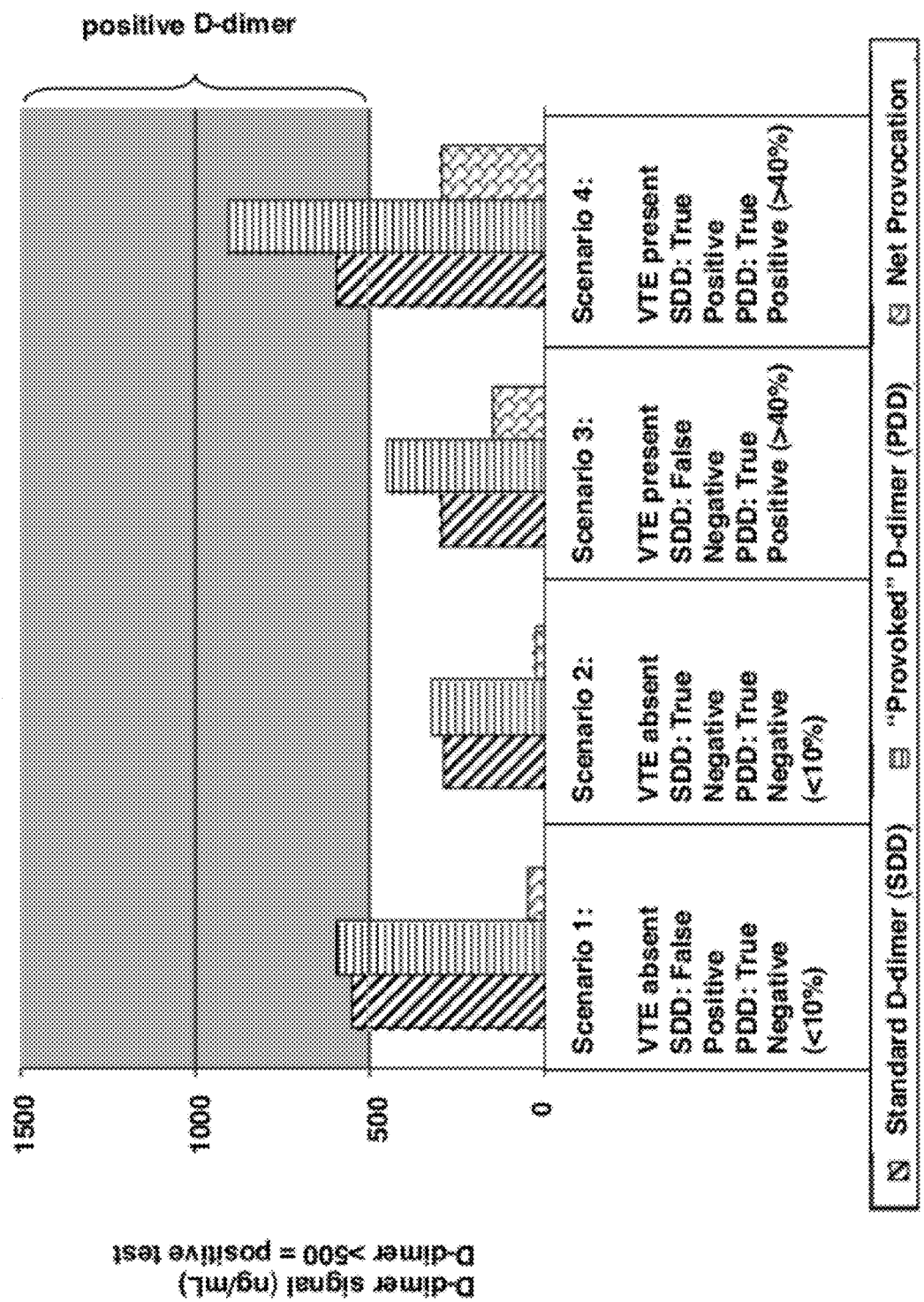
FIG. 5 depicts anticipated results showing net provocation variation in false positive, true negative, false negative, and true positive D-dimer results.

As shown in FIG. 5, in patients without pulmonary embolism or venous thromboembolism, "provoked" D-dimer levels are increased minimally, if at all (<10% of the SDD value) due to the absence of a clot. Therefore, in this situation regardless of the SDD value, either false positive or true negative (see scenario 1 and 2 in FIG. 5), the "provoked" D-dimer is amplified only minimally (i.e. negative "provoked" D-dimer test). Thus, the "provoked" D-dimer test will help to identify false positive standard D-dimer tests found commonly in many conditions (i.e. improvement in specificity) without loss of true negative standard D-dimer tests.

Similarly, as shown in FIG. 5, in patients with pulmonary embolism or venous thromboembolism, the "provoked" D-dimer signal is amplified significantly (approximately 40% above Standard D-dimer) due to enhanced clot lysis by exogenous t-PA. Therefore, in this situation regardless of the standard D-dimer value, either false negative or true positive (see scenario 3 and 4 in FIG. 5), the "provoked" D-dimer value is amplified significantly (i.e. positive "provoked" D-dimer). Thus the "provoked" D-dimer will help to correct false negative standard D-dimer tests without any loss of true positive standard D-dimer tests, thereby increasing the sensitivity.

Figure 6:
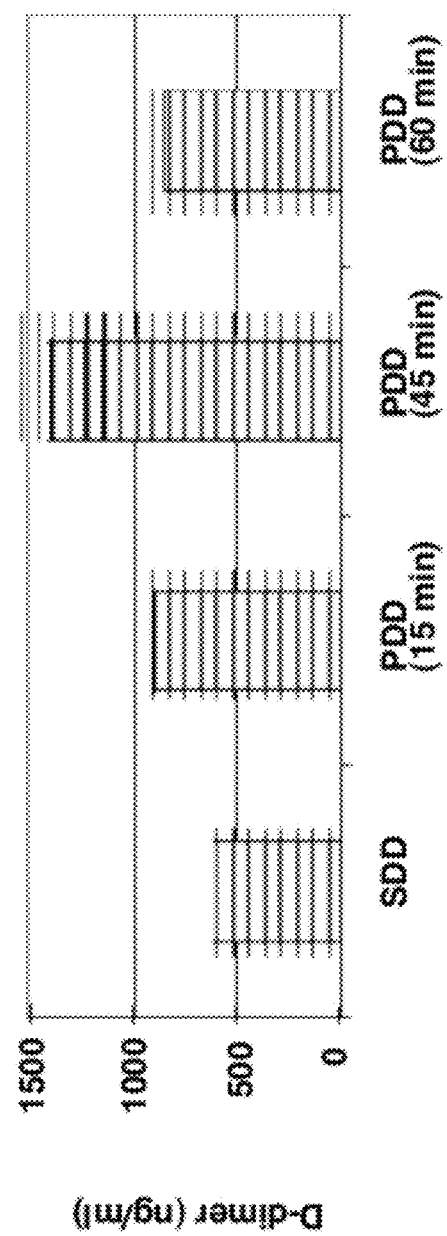
FIG. 6 depicts anticipated results showing the time response in vivo provocation.
Figure 7:
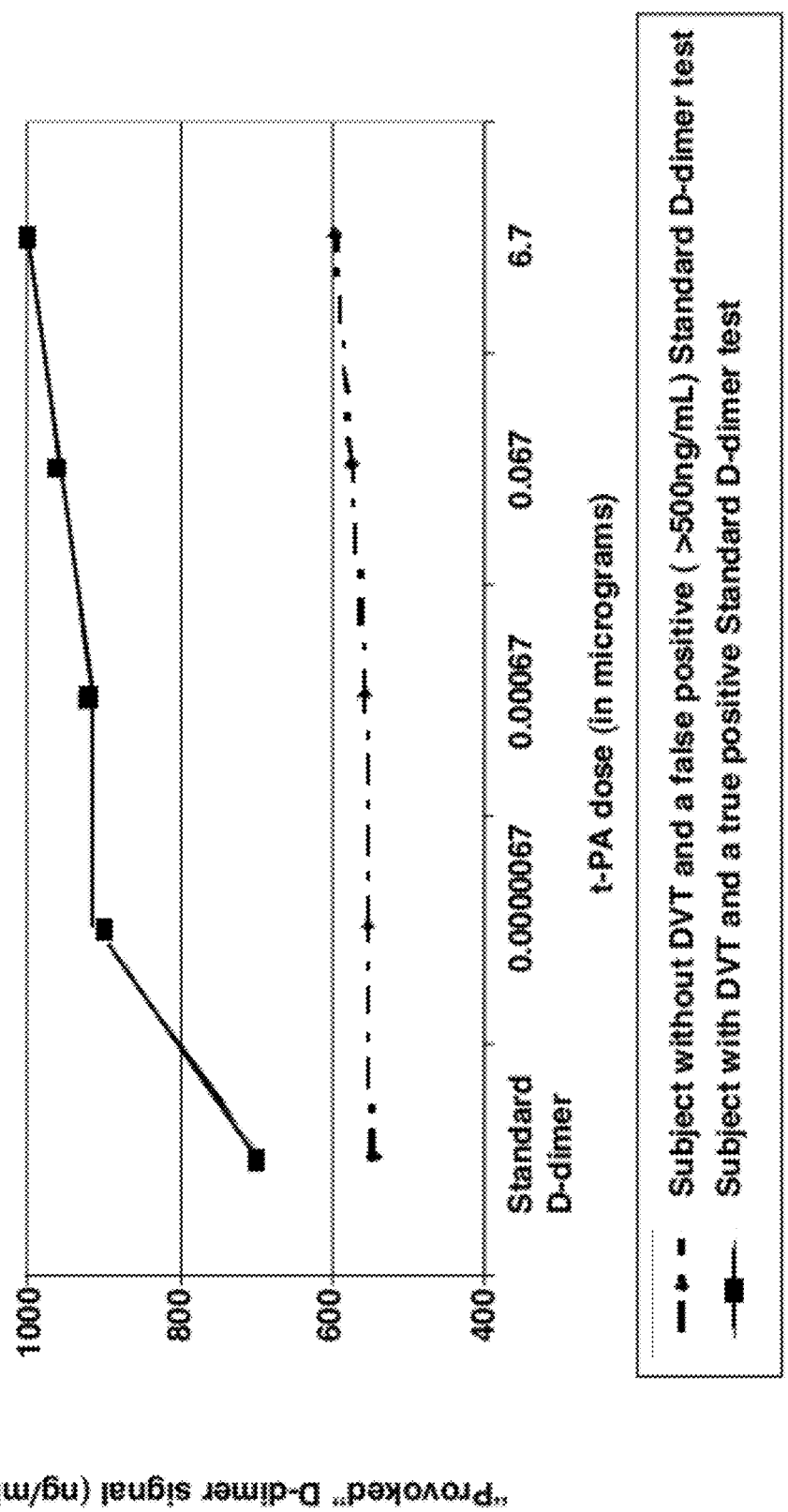
FIG. 7 shows the anticipated provocation of false positive (scenario 1) and true positive (scenario 4) standard D-dimer tests when variable dosages of t-PA are administered.
Figure 8:
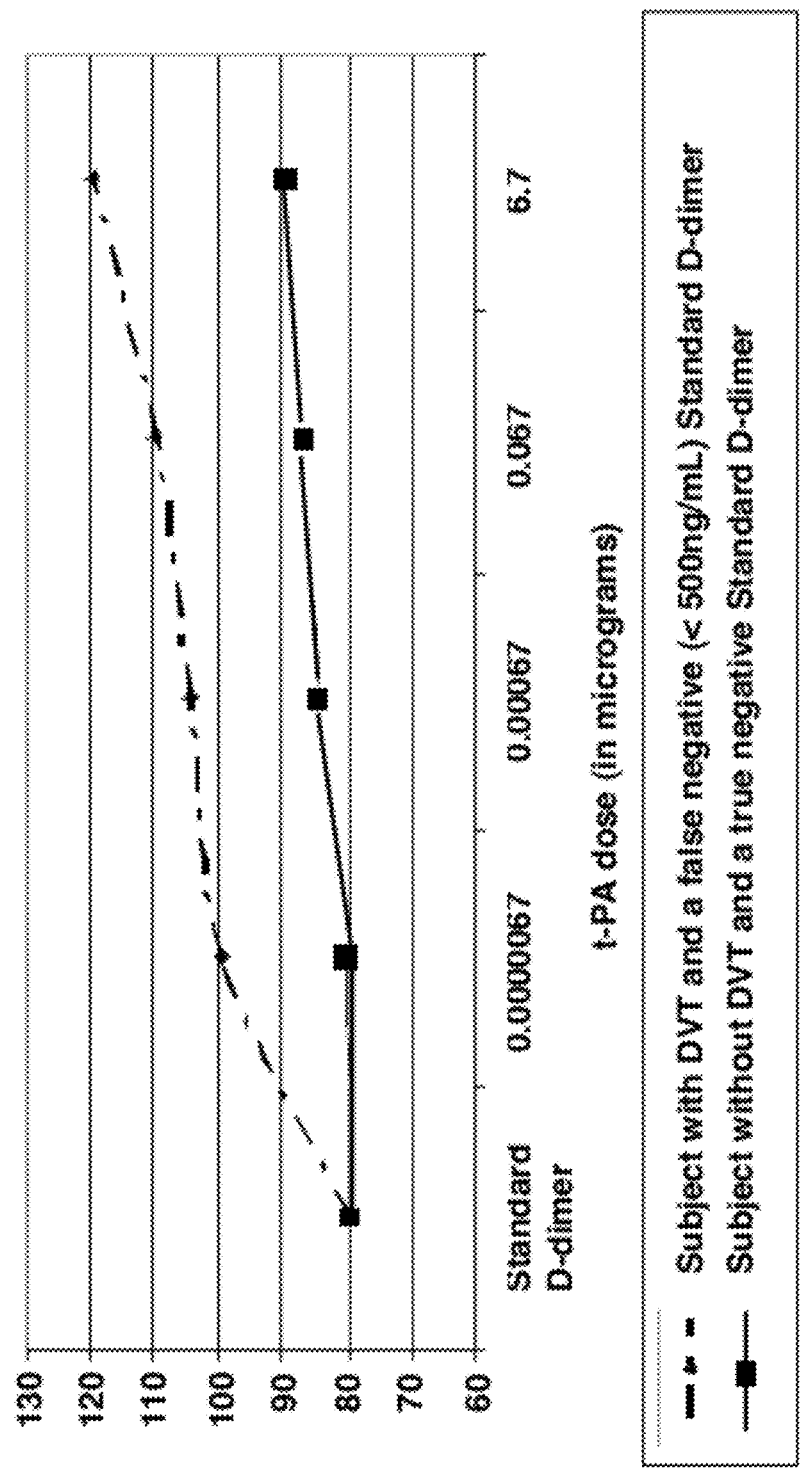
FIG. 8 depicts anticipated provocation of false negative (scenario 3) and true negative (scenario 2) standard D-dimer tests when variable dosages of t-PA are administered.
Figure 9:
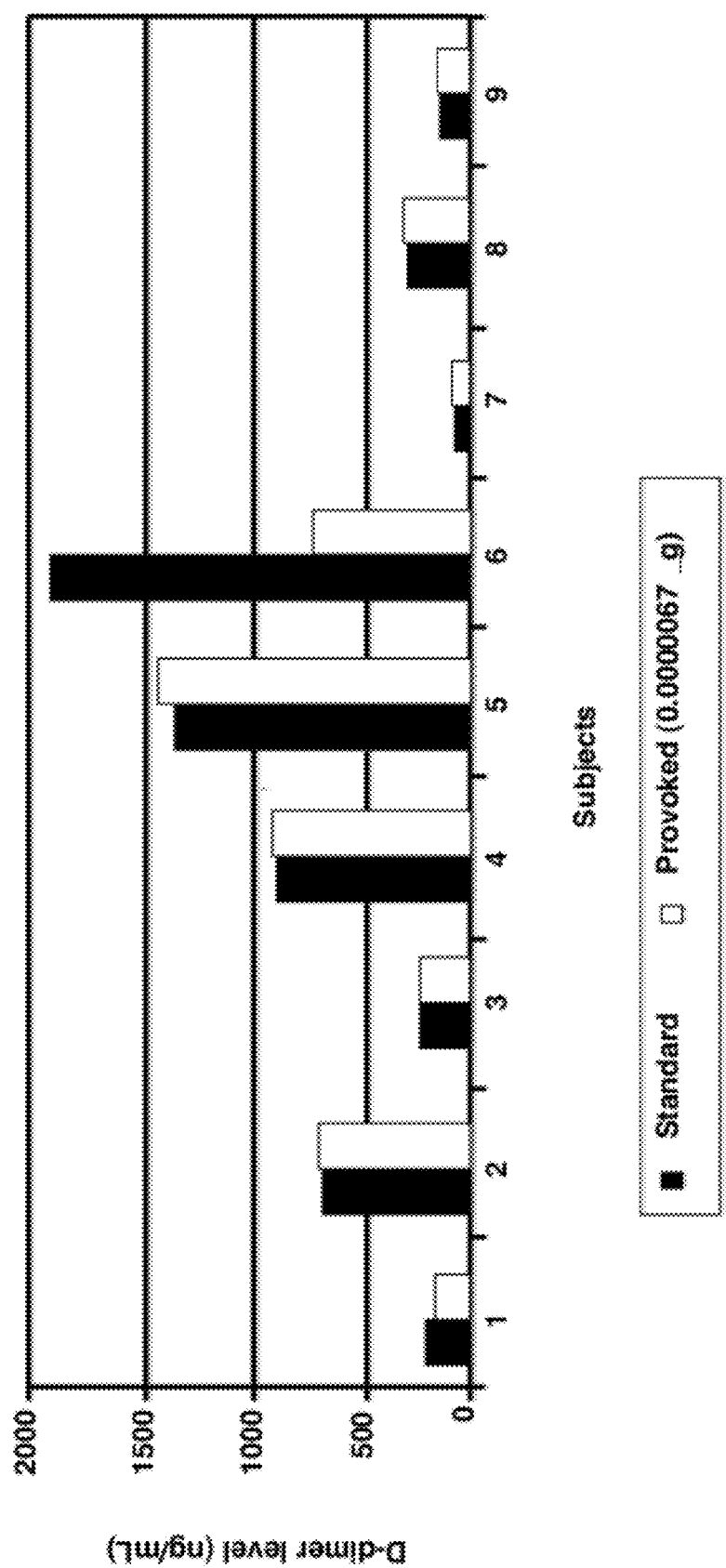
FIG. 9 shows a dose response of D-dimer levels to t-PA (in vitro) of plasma from patients without PE.
Figure 10:
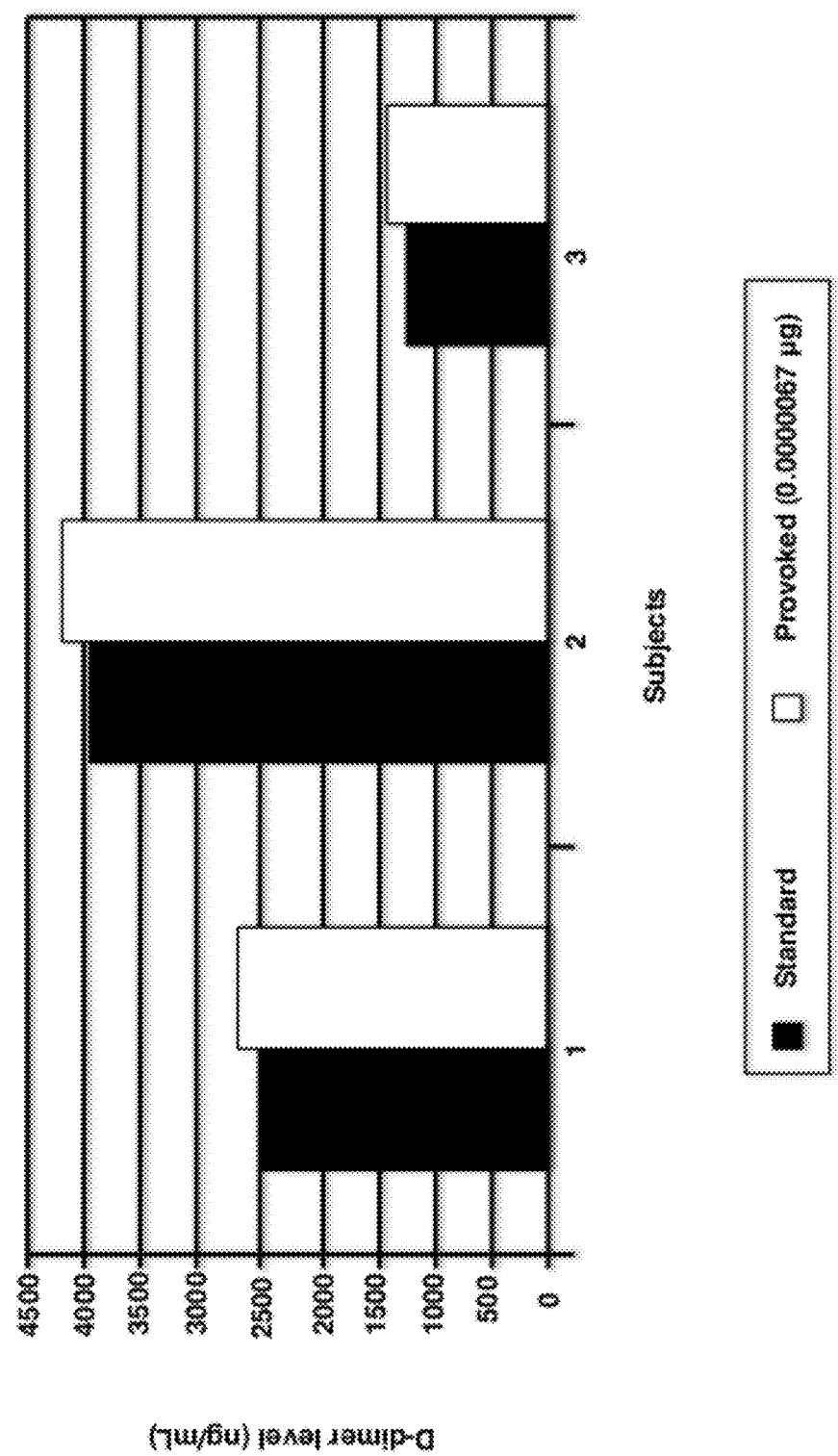
FIG. 10 shows a dose response of D-dimer levels to t-PA (in vitro) of plasma from patients with PE.

The anticipated results for time response to in vivo provocation are shown in FIG. 6. In the presence of a fibrin clot, exogenous t-PA significantly amplifies the D-dimer signals due to enhanced thrombolysis. Therefore, all 3 in vivo "provoked" D-dimer levels are higher than the baseline standard D-dimer value as shown in FIG. 6. In the presence of a fresh fibrin clot, the provocation is highest (up to 150% of the SDD value) at 45 minutes post t-PA, based on the swine study. This may vary in individuals based on clot composition, age of the clot and D-dimer clearance. The various anticipated dose response curves of each of the four scenarios described in FIG. 5 are displayed in FIGS. 7 and 8.

Beyond the preliminary data in humans, little is known about the D-dimer provocation by t-PA and its application in the diagnosis of PE/VTE in humans. The minimal effective dose of t-PA required for optimal D-dimer signal amplification is unknown in humans, therefore it may be tempting to perform a preliminary study to establish such a dose for D-dimer signal provocation. Such a study would be inappropriate as the researchers would have to expose human subjects to several different doses of t-PA in the search for the optimal dose for provocation.

ELISA Variability:

The test to test variability in the D-dimer ELISA assay may affect the data interpretation. As a solution, we will draw triplicates of the D-dimer assays and use the average of three D-dimer assays for each D-dimer result. Outliers (>20%) from each triplicate will be discarded.

Effect of Heparin on D-Dimer Levels:

In a study by Couturaud et al [58], use of heparin in 55 patients with venous thromboembolism was shown to decrease the standard D-dimer signal by an average of 25% in the first 24 hours of treatment. This resulted in a 6.2% loss in sensitivity of the Standard D-dimer test in diagnosing venous thromboembolism. Therefore, any participant who has been started on heparin treatment prior to enrollment may have reduced D-dimer levels due to prolonged heparin infusion. Note that the standard D-dimer test and the last "provoked D-dimer" test (i.e. at 60 minutes post t-PA) will be drawn within 2 hours of each other. If the attending physician decides to treat the patient with heparin, we will wait for 6 hours after initiation of heparin to draw our first D-dimer test (standard D-dimer) and therefore all (standard and "provoked D-dimer") tests will be drawn either without or with heparin at a steady state. Hence, heparin anticoagulation should affect both standard D-dimer as well as "Provoked" D-dimer assays equally and therefore should not affect the overall study outcome.

In another embodiment of the present invention, the following methods are contemplated. To amplify the D-dimer signal, exogenous administration of a bolus of t-PA in vivo should enhance the amounts of available tetramers and trimers from mature clot lysis. Subsequent in vitro PDD testing will contain higher D-dimer signals in cases of true cross linked fibrin clot. In the laboratory, a marked increase in the in vitro PDD levels were observed 36 hours after receiving 100 mg of t-PA in a patient with heavy clot burden leading to massive pulmonary emboli. This maneuver, we believe, could result in amplification of D-dimer signals preferentially in patients with a true fibrin clot.

Low Sensitivity of PDD:

Failure to increase the D-dimer signal with in vitro t-PA in older persons (low sensitivity of PDD): In the event of failure to increase the signal, we will first inject 4 mg of t-PA intravenously for the in vivo experiment and then draw the sample of blood 30 minutes after t-PA administration to perform the in vitro experiment (instead of drawing in vitro sample before t-PA administration). This will allow compensation for reduced endogenous t-PA in older individuals by using exogenous t-PA bolus to increase the availability of trimers and tetramers in subjects blood. We have preliminary data on two patients with deep vein thrombosis where 2 mg of an in vivo bolus of t-PA provoked the D-dimer levels above the SDD signals significantly (20-100%).

In the clinical setting, the D-dimer test suffers from poor specificity (25%), leading to many false positives and thus requiring unnecessary, expensive, and potentially dangerous additional imaging studies to confirm the diagnosis of VTE.

To address the issue of poor specificity, the inventors contemplate that the "provoked" D-dimer (PDD) test more accurately detects true fibrin clots compared to the current standard D-dimer (SDD) test in humans. The "provoked D-dimer" is defined as the amplified baseline (standard) D-dimer signal due to administration of recombinant tissue-type plasminogen activator (t-PA) either in vivo or in vitro. The "provoked D-dimer" is defined as the amplified baseline (standard) D-dimer signal due to administration of recombinant tissue-type plasminogen activator (t-PA) either in vivo or in vitro.

Rationale to Overcome Existing Barriers in the Diagnosis of PE

Based on an in vitro pilot experiment in humans, it is believed that the "provoked" D-dimer test may be a better diagnostic tool for PE/VTE than the current standard D-dimer test by eliminating its deficiencies as explained below.

An abnormal D-dimer result is not sufficient to diagnose PE due to many false positive test results. With the "provoked" D-dimer test, only minor degree of amplification in the D-dimer signal is expected to occur in the absence of fibrin clot. It is expected that this amplification of standard D-dimer is significantly more in the presence of true fibrin clot. Thus, the "provoked" D-dimer test could be a useful test to exclude a false positive standard D-dimer test which is the most important limiting factor in the clinical utility of the standard D-dimer test.

D-dimer levels are abnormal in 95 percent of patients with PE. In five percent of the patients with true VTE, standard D-dimer remains falsely normal which may be due to an impaired ability of a subject to lyse any present clot effectively. There is also evidence that older persons have low endogenous tissue plasminogen activator levels resulting in lower sensitivity of the D-dimer test for DVT. Therefore, in elderly individuals, if there is true fibrin clot present, administration of t-PA should amplify the standard D-dimer signal significantly due to enhanced fibrinolysis. In this circumstance, it is believed that the "provoked" D-dimer test is useful in excluding false negative D-dimer tests.

Thus, the "provoked" D-dimer test appears to be useful in improving both the sensitivity and specificity of the standard D-dimer test in patients with suspected VTE. This novel approach has been developed using existing available technology and thrombolytic agents, explored in preliminary human studies, and has the potential to reduce morbidity and mortality in patients with VTE. This noninvasive test can be used to screen a frail, elderly population who are at increased risk and this test can reduce health care costs of VTE by reducing unnecessary tests e.g. CTAV.

Figure 16:
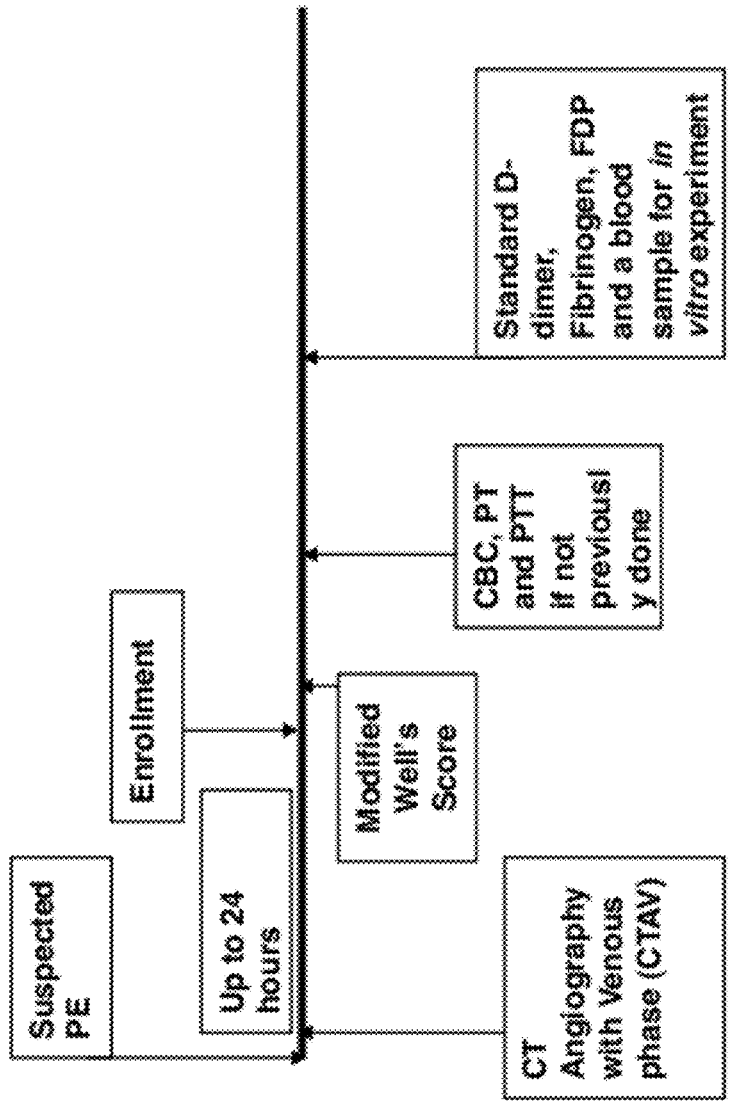
FIG. 16 illustrates the steps involved for provoked in vitro D-dimer experiments.

Research Design and Methods:

The following steps are performed in sequence, as follows:

In Vitro (FIG. 16)

1. Identify patients receiving CTAV for clinically suspected PE.
2. Obtain patient consent
3. Draw 12 mL of blood in a blue top test tube (citrated) for baseline D-dimer, CBC, PT, INR, PTT, fibrinogen, fibrinogen degradation products (FDP) tests and for in vitro D-dimer provocation.
4. Deliver blood samples to the lab supervisor to effect the blinded storage of the sample at −20° C.
5. Retrieve the numbered, blinded test tubes and thaw the samples in a body temperature water bath
6. Divide the samples into 5 equal aliquots for in vitro testing.
7. Place 0, 0.0000067, and 6.7 µg of t-PA in the aliquots, sequentially, and incubate for 1 hour.
8. Perform the ELISA D-dimer assay to determine the Standard D-dimer (SDD) level in the well with "0" µg of t-PA and the Provoked D-dimer levels in the wells with increasing t-PA concentration, in triplicate.
9. Perform statistical analyses to determine the optimal cut off value for highest sensitivity and specificity in identifying PE.

Figure 17:
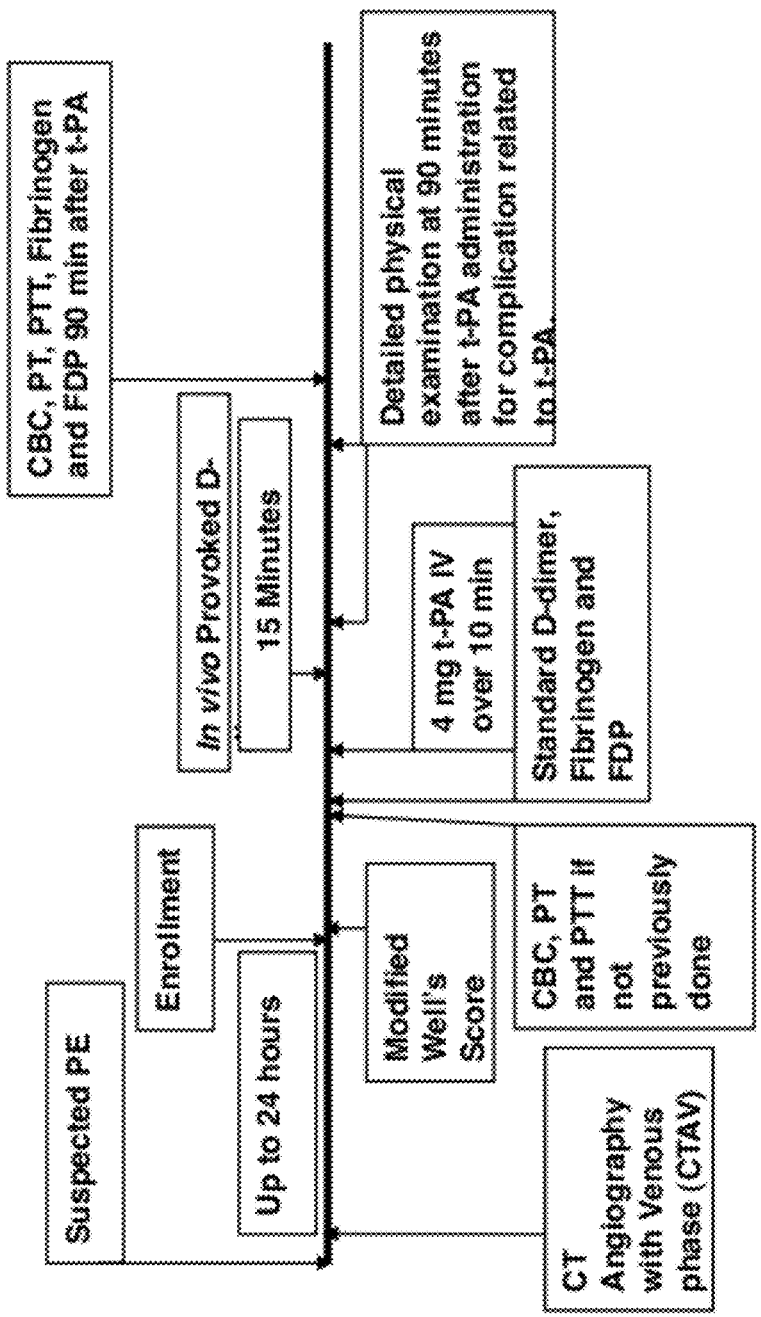
FIG. 17 illustrates the steps involved for provoked in vivo D-dimer experiments.

In Vivo (FIG. 17)

1. Identify patients receiving CTAV for clinically suspected PE.
2. Obtain patient consent
3. Draw 12 mL of blood in a blue top test tube (citrated) for baseline D-dimer, CBC, PT, INR, PTT, fibrinogen, and fibrinogen degradation products (FDP) tests
4. Inject 4 mg t-PA into the antecubital vein and flush with 5 ml of normal saline.
5. Draw 6 ml of citrated venous blood at 15 minutes after t-PA administration for in vivo provoked D-dimer levels and post provocation CBC, PT, INR, PTT, fibrinogen and FDP values at 90 minutes only.
6. Perform ELISA on post t-PA injection samples to obtain in vivo provoked D-dimer measurements at 15 minutes in triplicate.

7. Perform statistical analyses to determine the optimal cut off value for highest sensitivity and specificity in identifying PE.

Results

The results from 9 subjects without and 3 patients with PE are displayed below (Tables 3-9, FIGS. 9-15).

Figure 11:
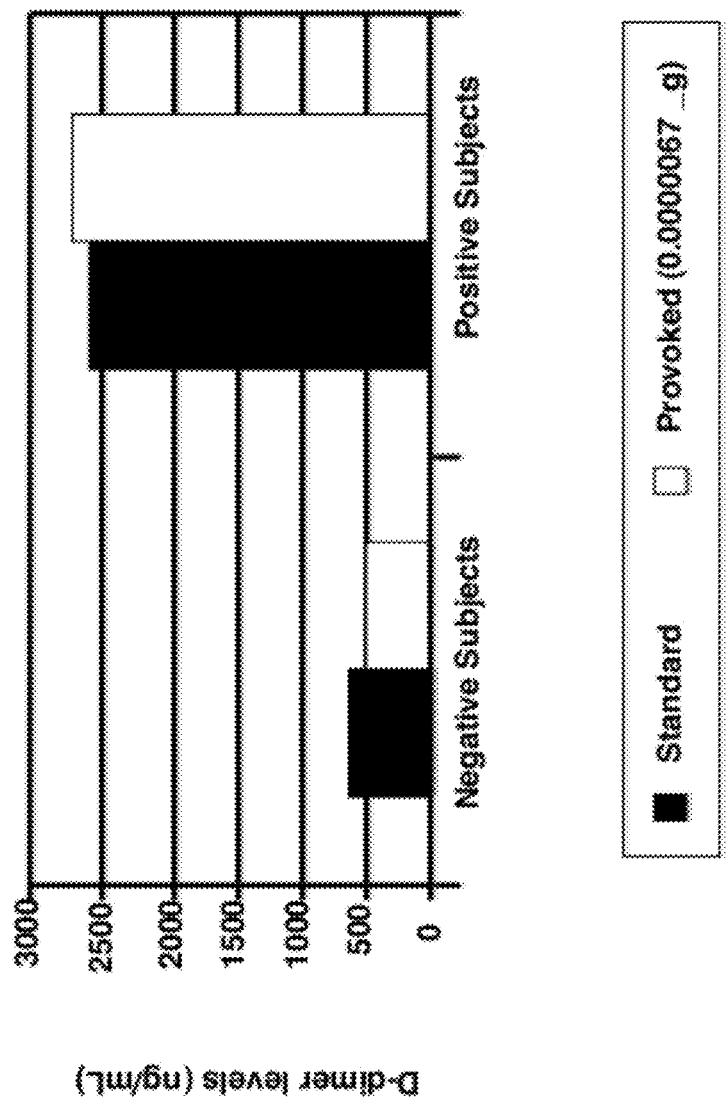
FIG. 11 shows a mean dose response of D-dimer levels to t-PA (in vitro) of plasma from patients with and without PE.
Figure 12:
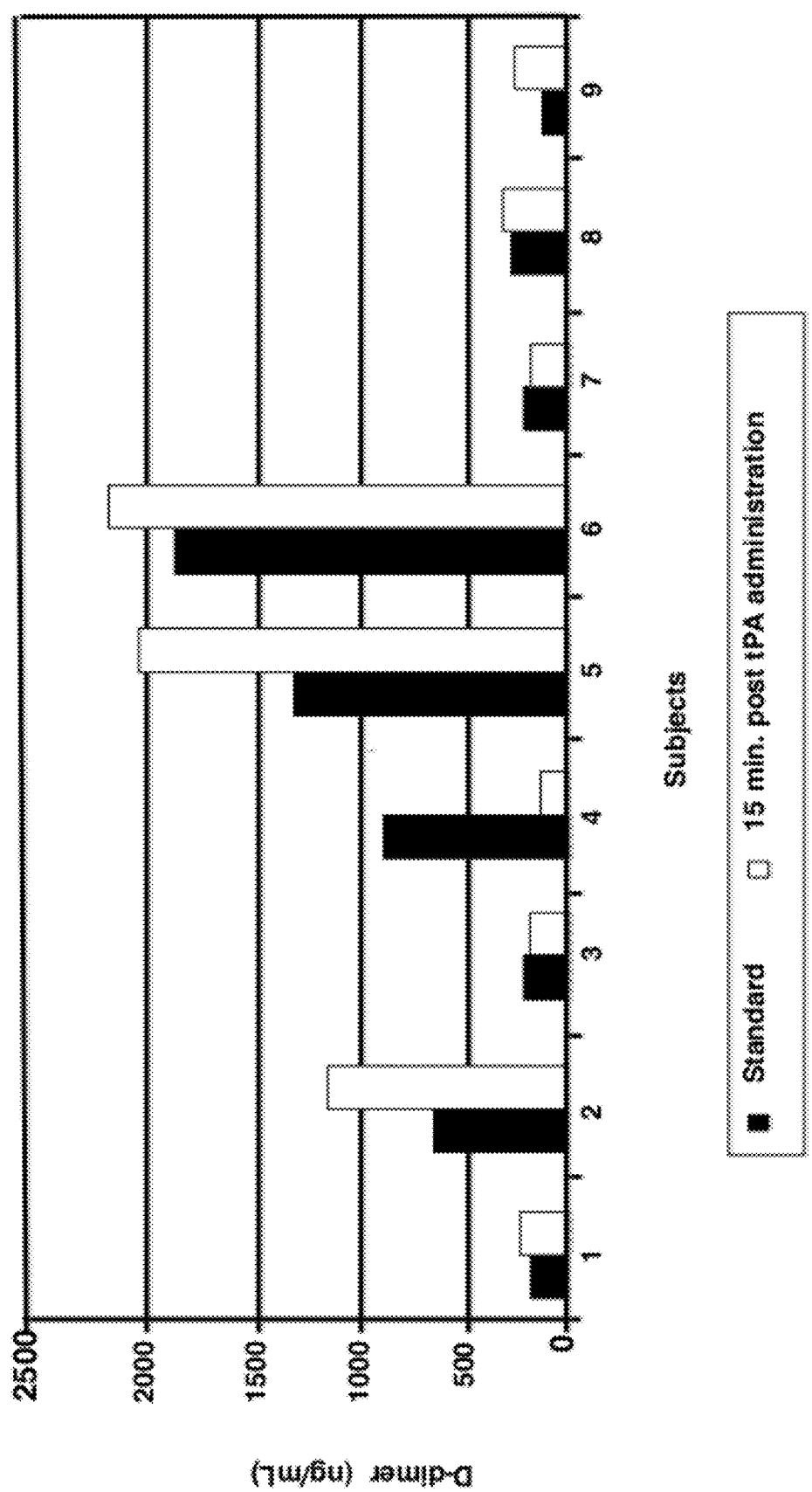
FIG. 12 shows a time response of D-dimer levels to t-PA (in vivo) of patients without PE.
Figure 13:
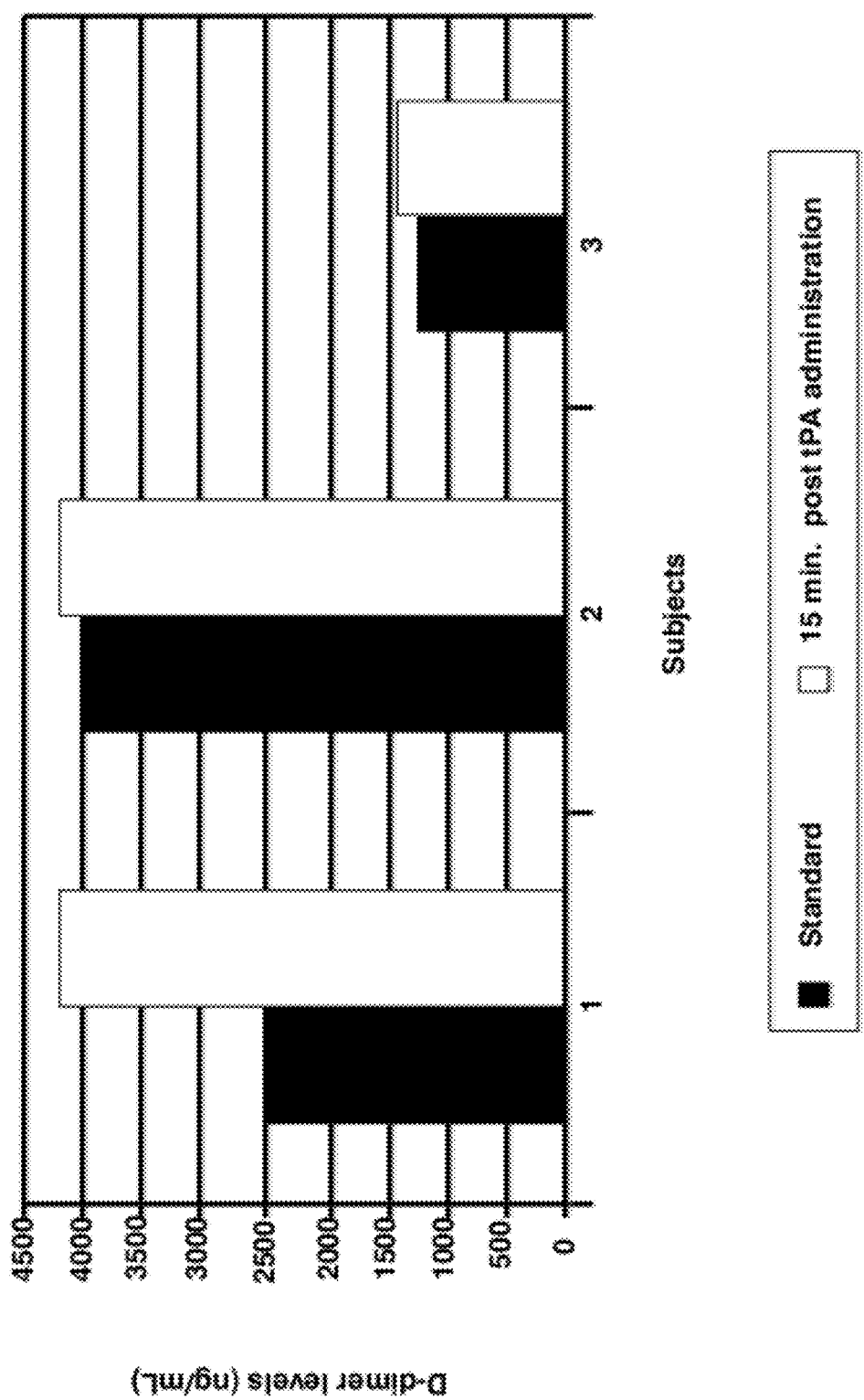
FIG. 13 shows a time response of D-dimer levels to t-PA (in vivo) of patients with PE.
Figure 14:
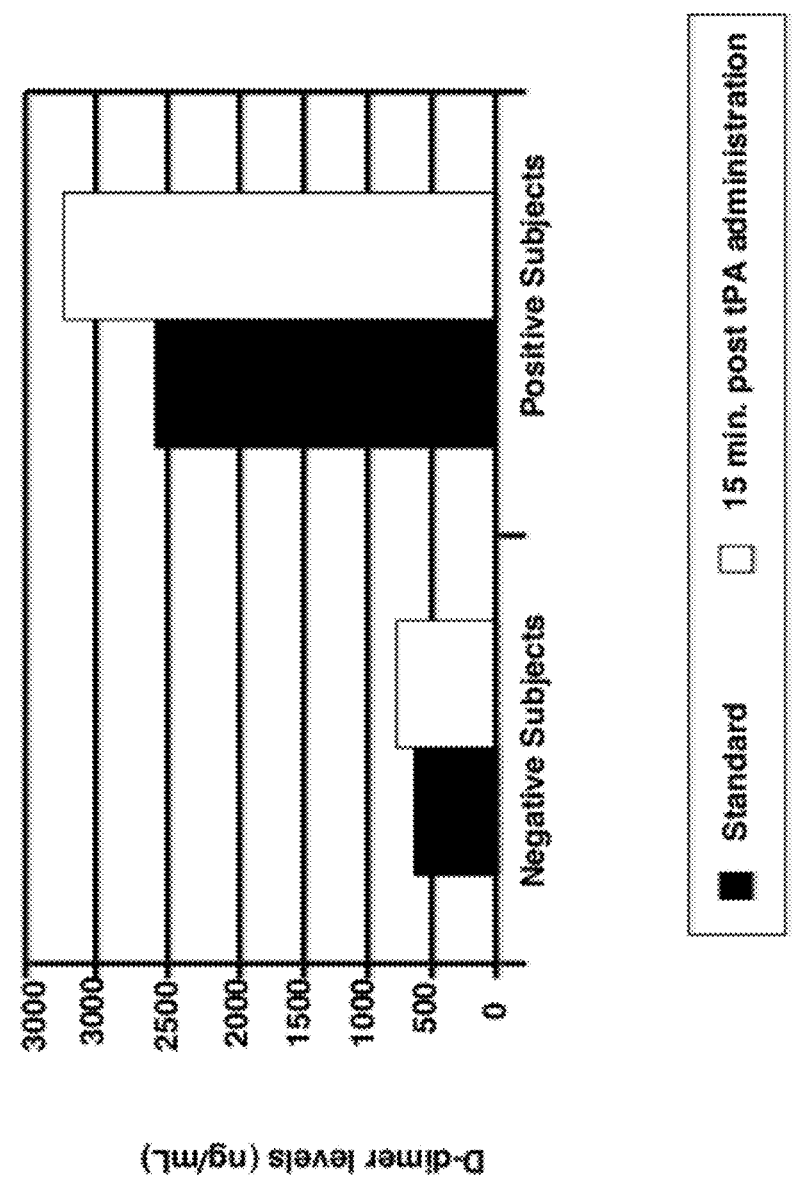
FIG. 14 shows a mean time response of D-dimer levels to t-PA (in vivo) of patients with and without PE.

The addition of exogenous t-PA to plasma from patients with PE resulted in significant increases in the mean D-dimer signal at doses 1 and 2, with the highest increase in the first dose (paired 1 tail t-test, p=0.001), while none of the dosages appreciably increased the mean D-dimer signal above the baseline in patients without PE (paired 1 tail t-test, p=0.204). The net provocation rose as exogenous tPA dose increased (FIG. 11).

The addition of exogenous t-PA to patients's bloodstream with PE resulted in statistically insignificant increases in the mean D-dimer signal at 15 minute post-tPA blood draw (paired 1 tail t-test, p=0.151). The post-tPA administration blood draws revealed increased D-dimer signals above the baseline in patients without PE at 15 minutes post-tPA administration (paired 1 tail t-test, p=0.243). The net provocation rose as time post-tPa administration increased (See FIG. 6).

Figure 15:
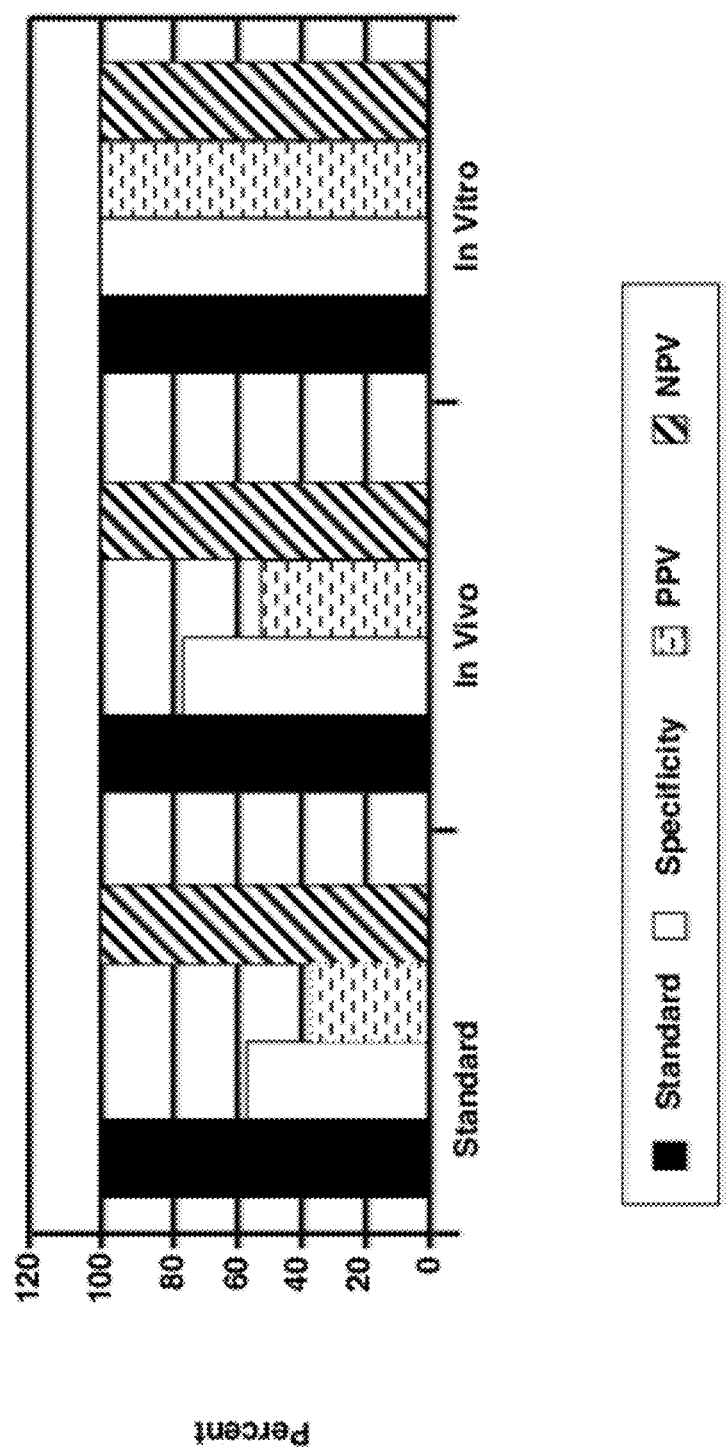
FIG. 15 shows truth table values of standard, in vitro and in vivo tests.

The truth tables using 178 ng/mL provocation cutoff values are displayed in tables 7-9 and FIG. 15. Notably, in this sample of patients, the standard D-dimer had a specificity of 58.33% and positive predictive value of 37.5%. The in vivo "Provoked" D-dimer test had a specificity of 75% and positive predictive value of 50%. The in vitro "Provoked" D-dimer test had a specificity of 100% and positive predictive value of 100%. All three tests had a sensitivity and negative predictive value of 100%.

The cutoff value of 178 ng/mL of absolute provocation of D-dimer signal was chosen as in the three subjects positive for PE, the minimal provocation was 179. This would preserve the inherent sensitivity of the D-dimer test while improving the specificity, as shown in the truth tables below.

TABLE 3

Dose response of D-dimer levels to t-PA (in vitro) of plasma from patients without PE

|  | Standard | Provoked 1 (0.0000067 µg) | Provoked 2 (6.7 µg) |
|---|---|---|---|
| D-dimer levels (ng/mL) | 193.498 | 155.384 | 140.947 |
|  | 654.72 | 673.19 | 519.838 |
|  | 224.24 | 234.306 | 238.156 |
|  | 881.2437 | 891.2165 | 674.104 |
|  | 1309.168 | 1407.083 | 2030.838 |
|  | 1880.339 | 711.502 | 302.8202 |
|  | 55.1352 | 69.2028 | 112.5779 |
|  | 286.998 | 297.914 | 554.736 |
|  | 133.227 | 138.042 | 178.492 |
| Averages | 624.2855 | 508.649 | 528.0565 |
| p-values |  | 0.204 | 0.327 |

TABLE 4

Dose response of D-dimer levels to t-PA (in vitro) of plasma from patients with PE

|  | Standard | Provoked 1 (0.0000067 µg) | Provoked 2 (6.7 µg) |
|---|---|---|---|
| D-dimer levels (ng/mL) | 2473.59 | 2684.213 | 2629.506 |
|  | 3964.756 | 4161.702 | 4009.303 |
|  | 1254.246 | 1430.42 | 1353.471 |
| Averages | 2564.197 | 2758.778 | 2664.093 |
| p-values |  | 0.001 | 0.045 |

TABLE 5

Time response of D-dimer levels to t-PA (in vivo) of patients without PE

| D-Dimer levels (ng/mL) | 193.498 | 233.6115 |
|---|---|---|
|  | 654.72 | 1156.935 |
|  | 224.24 | 174.42 |
|  | 881.2437 | 149.277 |
|  | 1309.168 | 2034.464 |
|  | 1880.339 | 2204.909 |
|  | 221.6018 | 179.9852 |
|  | 286.998 | 305.939 |
|  | 133.227 | 244.302 |
| Averages | 642.7818 | 742.6492 |
| p-values |  | 0.243 |

TABLE 6

Time response of D-dimer levels to t-PA (in vivo) of patients with PE

|  | Standard | 15 Minutes |
|---|---|---|
| D-Dimer levels (ng/mL) | 2473.59 | 4192.182 |
|  | 3964.756 | 4173.425 |
|  | 1254.246 | 1433.03 |
| Averages | 2808.296 | 3266.212 |
| p-values |  | 0.151 |

TABLE 7

Truth table for standard D-dimer

|  | True clot | False clot | Positive/Negative predictive value |
|---|---|---|---|
| Test positive | 3 | 5 | 37.5% |
| Test negative | 0 | 7 | 100% |
| Sen/Spec | 100% | 58.33% |  |

TABLE 8

Truth Table in vitro for "Provoked" D-dimer (Dosage = 0.0000067 µg/mL, Cutoff = 178 ng/mL provocation)

|  | True clot | False clot | Positive/Negative predictive value |
|---|---|---|---|
| Test positive | 3 | 0 | 100% |
| Test negative | 0 | 12 | 100% |
| Sen/Spec | 100% | 100% |  |

TABLE 9

Truth Table in vivo for "Provoked" D-dimer (15 minutes post tPA administration, Cutoff = 178 ng/mL provocation)

|  | True clot | False clot | Positive/Negative predictive value |
|---|---|---|---|
| Test positive | 3 | 3 | 50% |
| Test negative | 0 | 9 | 100% |
| Sen/Spec | 100% | 75% |  |

Thus, in accordance with the above-described disclosure, the present invention is directed to a method of diagnosing a venous thromboembolism or intracardiac thrombi in an individual in need of such treatment, comprising the steps of: obtaining a plasma sample from said individual; determining the baseline level of D-dimer in said sample; contacting said sample with a compound that catalyzes the conversion of plasminogen into plasmin; and measuring the level of D-dimer is said sample after contacting said sample with a compound that catalyzes the conversion of plasminogen into plasmin, wherein a significantly greater concentration of D-dimer after contact with a compound that catalyzes the conversion of plasminogen into plasmin than prior to contact with a compound that catalyzes the conversion of plasminogen into plasmin indicates that the individual has pulmonary embolism or venous thromboembolism. Representative compounds that catalyze the conversion of plasminogen into plasmin include, but are not limited to tissue plasminogen activator, reteplase, tenecteplase, anistreplase, streptokinase, staphylokinase, urokinase and any other thrombolytic agent known to those of ordinary skill in this art. This concentration of the compound used may be related to various factors, including the nature of specific compound but generally, a person having ordinary skill in this art would be able to readily determine a useful concentration of the compounds that catalyze the conversion of plasminogen into plasmin. For example, when the compound is tissue plasminogen activator, it may be used to contact the sample in a dose of from about 0.01 micrograms to about 10 micrograms. Generally, the D-dimer may be measured using any assay known in the art, such as an enzyme linked immunosorbent assay, the latex agglutination assay or the D-dimers may be measured using anti-D-dimer monoclonal antibody.

The present invention is further directed to a method of diagnosing a pulmonary embolism or venous thromboembolism in an individual in need of such treatment, comprising the steps of: obtaining a plasma sample from the individual; determining the baseline level of D-dimer in the sample; administering a compound that catalyzes the conversion of plasminogen into plasmin to the individual; and measuring the level of D-dimer is the sample after contacting the sample with a compound that catalyzes the conversion of plasminogen into plasmin, wherein a significantly greater concentration of D-dimer after contact with a compound that catalyzes the conversion of plasminogen into plasmin than prior to contact with a compound that catalyzes the conversion of plasminogen into plasmin indicates that the individual has pulmonary embolism or venous thromboembolism. As described above, representative compounds are described above (such as tissue plasminogen activator, reteplase, tenecteplase, anistreplase, streptokinase, urokinase, and other thrombolytic agents and preferably the compound is administered in a dose of from about 1 milligram to about 10 milligrams. In a preferred embodiment, the compound is tissue plasminogen activator and the tissue plasminogen activator is administered in a dose of about 4 milligrams. Depending upon the compound used, the compound may be administered as would be well known in the art. For example, tissue plasminogen activator is administered intraveneously.

The present invention is further directed to a kit for diagnosing a venous thromboembolism or intracardiac thrombi in an individual using a method according to claim 1, comprising: anti-D-dimer monoclonal antibodies; a compound that catalyzes the conversion of plasminogen into plasmin; and if appropriate a negative control sample. The compound may be selected from the group consisting of tissue plasminogen activator, reteplase, tenecteplase, anistreplase, streptokinase, urokinase. Anti-D-dimer monoclonal antibodies are known to those of ordinary skill in this art.

One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method of diagnosing venous thromboembolism or intracardiac thrombi in a human individual, comprising the steps of:
    determining a baseline blood concentration level of D-dimer in a blood sample obtained from the individual;
    contacting the sample obtained from the individual or an aliquot thereof with an effective amount of streptokinase to degrade soluble fibrin in the blood sample or aliquot thereof to produce a D-dimer concentration that is increased over the baseline blood level of D-dimer; and
    measuring the concentration of D-dimers in the sample contacted with streptokinase, wherein a difference between the concentration of D-dimer in the blood sample contacted with the streptokinase and the baseline D-dimer concentration that is greater by at least 178 ng/ml indicates that the individual has pulmonary embolism or venous thromboembolism, and wherein the D-dimer concentrations are measured using an enzyme linked immunosorbent assay or latex agglutination assay.

2. The method of claim 1, wherein the D-dimers are measured using an anti-D-dimer monoclonal antibody.

3. The method of claim 1, wherein the venous thromboembolism is a pulmonary embolism.

* * * * *